(12) United States Patent
Shih et al.

(10) Patent No.: US 8,597,693 B2
(45) Date of Patent: Dec. 3, 2013

(54) PHARMACEUTICAL COMPOSITION WITH IMMUNOMODULATING FUNCTION

(75) Inventors: Ying-Chu Shih, Zhubei (TW); Lain-Tze Lee, Hsinchu (TW); Bie-Shung Tsai, Taipei (TW); Jir-Mehng Lo, Guanxi Township, Hsinchu County (TW); Tien-Soung Tong, Hsinchu (TW); Jenn-Line Sheu, Hsinchu (TW); Kuo-Kuei Huang, Zhudong Township, Hsinchu County (TW); Ying-Fei Tsai, Hsinchu (TW); Yi-Ching Lee, Hsinchu (TW); Hui-Ju Liang, Taipei (TW); Jui-Hung Yen, Luzhou (TW); Cheng-Yu Lee, Hsinchu (TW)

(73) Assignee: Industrial Technology Research Institute, Hsinchu County (TW)

( * ) Notice: Subject to any disclaimer, the term of this patent is extended or adjusted under 35 U.S.C. 154(b) by 322 days.

(21) Appl. No.: 12/829,357

(22) Filed: Jul. 1, 2010

(65) Prior Publication Data
US 2012/0003250 A1 Jan. 5, 2012

(51) Int. Cl.
A01N 65/00 (2009.01)

(52) U.S. Cl.
USPC .......................................................... 424/725

(58) Field of Classification Search
None
See application file for complete search history.

(56) References Cited

U.S. PATENT DOCUMENTS 7,348,032 B2 * 3/2008 Lin et al. ........................ 424/725
2009/0280200 A1 * 11/2009 Pan et al. ....................... 424/757

FOREIGN PATENT DOCUMENTS

| CN | 1686423 A | 10/2005 |
| CN | 1899333 A | 1/2007 |
| CN | 1994378 A | 7/2007 |
| CN | 101333240 A | 12/2008 |

OTHER PUBLICATIONS

Woo et al., Arch. Pharm. res., vol. 16, No. 1, pp. 29-31, 1993.*
Xu et al., International Immunopharmacology, 7, 2007, 175-182.*
Feldmann et al., "Discovery of TNF-α as a therapeutic target in rheumatoid arthritis: preclinical and clinical studies", Joint Bone Spine 2002; 69:12-8.
Charles et al., "Regulation of Cytokines, Cytokine Inhibitors, and Acute-Phase Proteins Following Anti-TNF-(alpha) Therapy in Rheumatoid Arthritis", J. Immunol. 1999;163,1521-1528.
Estevez-Braun et al., "Busaliol and Busalicifol, Two New Tetrahydrofuran Lignans From Bupleurum Salicifolium", Journal of Natural Products, vol. 58, No. 6, pp. 887-892, Jun. 1995.
Estevez-Braun et al., "Antibiotic Activity and Absolute Configuration of SS-Heptadeca-2(Z),9 (Z)-Diene-4,6-Diyne-1,8-Diol From Bupleurum Salicifolium", Journal of Natural Products, vol. 57, No. 8, pp. I178-1182, Aug. 1994.
Partial European search report issued by the European Patent Office on Dec. 7, 2010, for the instant U.S. application's counterpart application filed in the European Patent Office.
Woo et al., "Antiinflammatory Principle of Bupleurum Iongiradiaturn Roots", Arch. Pharm. Res., vol. 16, No. 1, pp. 29-31, 1993.
Cheng et al., "Macrophage immunomodulatory activity of the polysaccharides from the roots of *Bupleurum smithii* var. parvifolium", Journal of Ethnopharmacology, 130 (2010), 363-368, Elsevier Scientific Publishers Ltd.
Gonzalez et al., "Biological activity of secondary metabolites from *Bupleurum salicifolium* (Umbelliferae)", Experientia 51 (1995), pp. 35-39, Birkhaeuser Verlag, Basel, CH.
Gonzalez et al., "Isokaerophyllin, a butyrolactone from Bupleuru Salicifolium", Phytochemistry, vol. 9, No. 2, pp. 675-678, 1990, Pergamon Press, GB.
Yang et al., "ITS sequence analysis used for molecular identification of the *Bupleurum* species from northwestern China", Phytomedicine, 14 (2007) 416-423, Gustav Fischer Verlag, Stuttgart, DE.
Chang et al., "Immunosuppressive flavones and lignans from *Bupleurum scorzonerifolium*" Phytochemistry, 64 (2003), 1375-1379, Pergamon Press, GB.
Anonymous, "Altai *Bupleurum*", Online Wikipedia info from Internet, Nov. 9, 2010.
Yang et al., "Flavonoids in Altai Chaihu" Journal of Beijing University of Traditional Chinese Medicine, vol. 33, No. 3 (2010) 207-209.
Yang et al., "Chemical components in volatile oil from Altai *Bupleurum* root", Journal of Beijing University of Traditional Chinese Medicine, vol. 28, No. 6 (2005) 63-65.
Sheh et al., "Bubleurum Linnaeus, Sp. Pl. 1:236, 1753", Flora of China, 14: 60-74, 2005.
Database WPI Week 200805, Thomson Scientific, London; GB; AN 2008-A60306 XP002600610.
Notification of second examination opinion issued by the China Intellectual Property Office on Jun. 5, 2012, for the above-referenced application's counterpart application in China (Application No. 200910265504.5).

(Continued)

*Primary Examiner* — Michael Meller
(74) *Attorney, Agent, or Firm* — Pai Patent & Trademark Law Firm; Chao-Chang David Pai

(57) ABSTRACT

A pharmaceutical composition with an immunomodulating function is provided, including an extract of *Bupleurum* obtained by grinding the *Bupleurum*, adding the ground *Bupleurum* to a solvent and isolating the extract from the solvent, wherein the *Bupleurum* comprises *Bupleurum krlovianum*, *Bupleurum longiradiatum*, *Bupleurum smithii*, *Bupleurum pusillum*, *Bupleurum longicaule*, *Bupleurum salicifolium*, *Bupleurum scorzonerifolium* and Bupleurums with at least one of the nucleotide sequences selected from a group consisting of SEQ ID NOs. 1~6 and a nucleotide sequence with no more than 1% of the nucleotide sequence divergences of SEQ ID NOs. 1~6, or combinations thereof.

1 Claim, 17 Drawing Sheets

(56) References Cited

OTHER PUBLICATIONS

Xie et al, "Inhibition of saikosaponin-a on intracellular free calcium concentration and interleukin-6 release in hippocampal astrocytes activated by glutamate", Journal of Beijing University of Traditional Chinese Medicine, vol. 31, No. 11, Nov. 2008.

Notification of first examination opinion issued by the China Intellectual Property Office on Sep. 16, 2011, for the above-referenced application's counterpart application in China (Application No. 200910265504.5).

Sun et al., "Digitized fingerprint of Radix Bupleuri by HPLC", Central South Pharmacy, vol. 5, No. 1, 79-82, Feb. 2007.

Xie, "Discussion in Plant Systematics for *Bupleurum* Species Based on ITS Sequences and Preliminary Study on Species Differences in Comparative Protein Expression Profiles among Three *Bupleurum* Species", Fudan University, Shanghai, China, Ph.D. Dissertation, p. 9, Apr. 2006.

\* cited by examiner

PHARMACEUTICAL COMPOSITION WITH IMMUNOMODULATING FUNCTION

BACKGROUND

1. Technical Field

The disclosed relates to a pharmaceutical composition with an immunomodulating function, and in particular relates to an extract of *Bupleurum* with an immunomodulating function.

2. Description of the Related Art

The mechanism for immune disorders has been reported in several studies. Many studies indicate that the over-expressed tumor necrosis factor (TNF-$\alpha$) is related to immuno-inflammatory diseases, such as rheumatoid arthritis (RA), Crohn's disease, psoriatic arthritis or ankylosing spondylitis.

TNF-$\alpha$ functions like cytokines, modulates cell recruitment, cell proliferation, cell death and immune regulation. At low concentrations in tissues, TNF-$\alpha$ may augment host defense mechanisms against infection. At high concentrations, TNF-$\alpha$ results in excess inflammation leading to organ injuries. Thus, Brennan et al. reported that the removal of excess TNF from the sites of inflammation can treat the immune disorders caused by inflammatory responses (Brennan et al., 1989, Inhibitory effect of TNF-$\alpha$ antibodies on synovial cell interleukin-1 production in rheumatoid arthritis. *Lancet* 2, 244-247).

Feldmann et al. reported that TNF plays a particularly important role in the regulation of a cascade of pathogenic events in RA, Crohn's disease, psoriasis and other diseases, exemplified by the rapid induction of cytokines, such as IL-1$\beta$ and IL-6 (Feldmann et al., 2002, Discovery of TNF-$\alpha$ as a therapeutic target in rheumatoid arthritis: preclinical and clinical studies. *Joint Bone Spine* 69, 12-18). TNF is over-expressed particularly in animal models of RA (Keffer et al., 1991, Transgenic mice expressing human tumor necrosis factor: a predictive genetic model of arthritis. *EMBO J* 10, 4025-4031). It has been suggested that a dramatic reduction in serum IL-6 concentrations occurred within 1 day of infliximab therapy was a direct effect of TNF neutralization (Charles et al., 1999, Regulation of cytokines, cytokine inhibitors, and acute-phase proteins following anti-TNF-$\alpha$ therapy in rheumatoid arthritis. *J Immunol* 163, 1521-1528).

Many biologics with inhibition of TNF-$\alpha$ have been produced, such as adalimumab, etanercept, infliximab, DMARDs (for example, methotrexate), or NSAIDs. Due to fast drug efficacy, dramatic effects and well immune toleration, these biologics have become main stream market products. However, biologics are expensive, demanding intravenous administration and have adverse effects, such as risks of inducing undesired immune responses or infection. Developing a drug which is safe for the immune system is challenging.

*Bupleurum* is a genus of plants used in Chinese medicine for reducing fever, relieving pain, eliminating toxins and reducing inflammation. In Chinese medicine, *Bupleurum* primarily treats fullness and discomfort in the chest, bitterness in the mouth, dryness in the throat, alternate spell of chill and fever, jaundice, hepatitis, enterogastritis and cholecystitis. The root of *Bupleurum* is usually used. It has been reported that saikosaponin, longispinogenin, sterols, lipid oil, isoflavones and sugars were isolated from the root of a plant of *Bupleurum*, and saikosaponin was determined as the chief component. Saikosaponin a and d have been proved to have medicinal effects (Liu S. U., et al., Development Diversity of *Bupleurum*, *Journal of Agricultural Research of China*, v. 53, No. 2 (June, 2004)).

*Bupleurum* has been enthusiastically studied for hepatitis. However, there is no study or journal published implementing the application of *Bupleurum* to immunomodulation. The inventors have studied the extraction of *Bupleurum*, wherein the active ingredient of the extract was identified, and the relationship between the active ingredient and TNF-$\alpha$ or IL-6 in vivo was determined. Finally, a novel pharmaceutical composition with an immunomodulation has been developed.

SUMMARY

A detailed description is given in the following embodiments with reference to the accompanying drawings.

The embodiment of invention provides a pharmaceutical composition with an immunomodulating function, comprising an extract of *Bupleurum* obtained by grinding the *Bupleurum*, adding the ground *Bupleurum* to a solvent and isolating the extract from the solvent, wherein the *Bupleurum* comprises *Bupleurum krlovianum*, *Bupleurum longiradiatum*, *Bupleurum smithii*, *Bupleurum pusillum*, *Bupleurum longicaule*, *Bupleurum salicifolium*, *Bupleurum scorzonerifolium* and Bupleurums with at least one of the nucleotide sequences selected from a group consisting of SEQ ID NOs. 1~6 and a nucleotide sequence with no more than 1% of the nucleotide sequence divergences of SEQ ID NOs. 1~6, or combinations thereof.

Another embodiment of invention further provides a pharmaceutical composition with an immunomodulating function, comprising kaerophyllin or cis-isomer as an active ingredient.

BRIEF DESCRIPTION OF THE DRAWINGS

The present invention can be more fully understood by reading the subsequent detailed description and examples with references made to the accompanying drawings, wherein.

DETAILED DESCRIPTION

Figure 1:
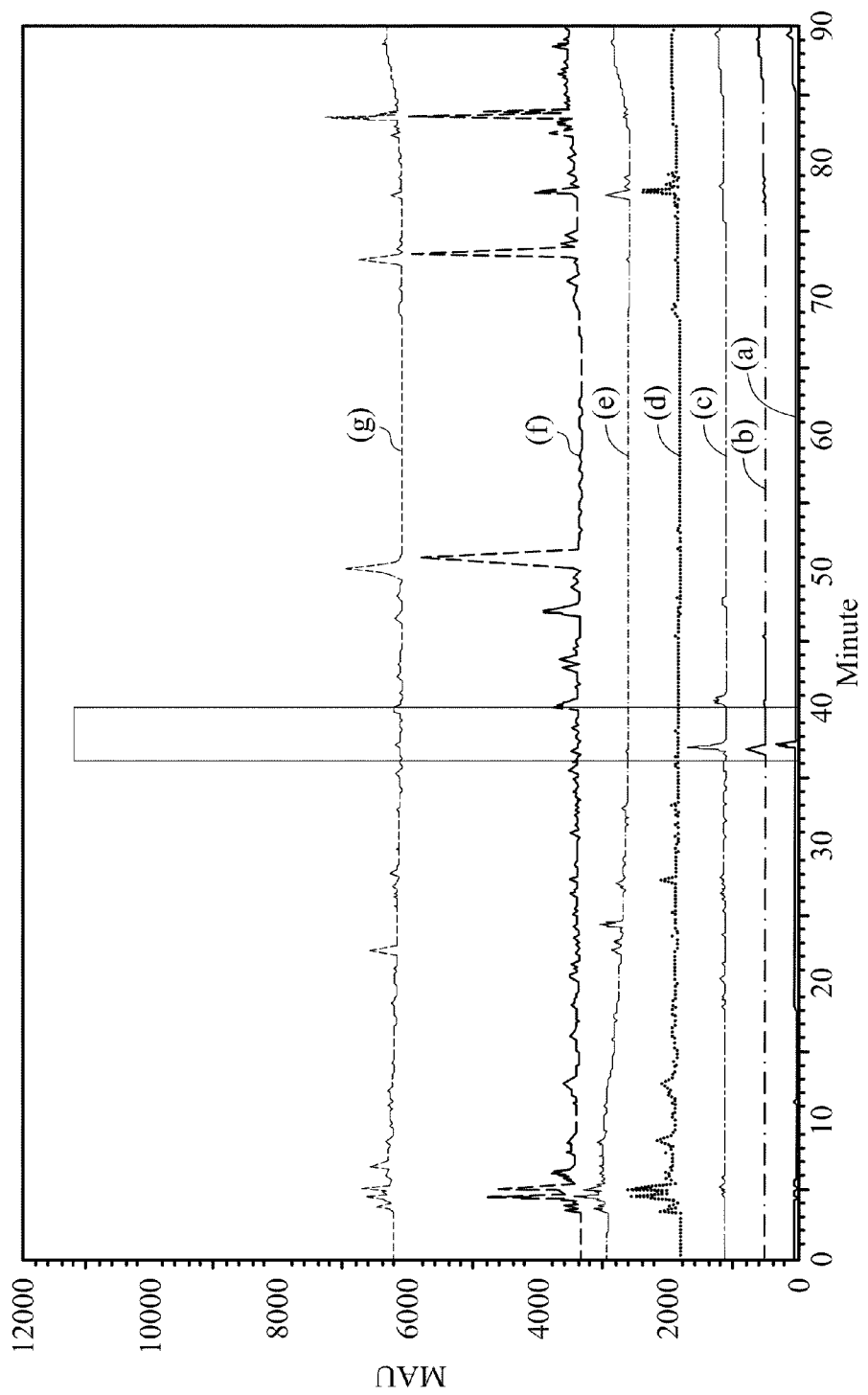
FIG. 1 is an HPLC chromatogram of the extracts of *Bupleurum* by a 95% ethanol aqueous solution.

The following description is of the best-contemplated mode of carrying out the invention. This description is made for the purpose of illustrating the general principles of the invention and should not be taken in a limiting sense. The scope of the invention is best determined by reference to the appended claims.

In one aspect, the embodiment of invention provides a pharmaceutical composition with an immunomodulating function, comprising an extract of *Bupleurum* by a solvent.

Specifically, the *Bupleurum* comprises *Bupleurum krlovianum*, *Bupleurum longiradiatum*, *Bupleurum smithii*, *Bupleurum pusillum*, *Bupleurum longicaule*, *Bupleurum salicifolium*, or *Bupleurum scorzonerifolium*.

While some medicinal plants are plentiful, some are not. Medicinal plants with similar morphology or names sometimes cause confusion, wherein they are interchanged. Traditional identification of medicinal plants require a skilled person, considering the plant morphology, and taste and performing microscopic examination. Once plants show similar morphology or lose their original taste, they are usually undistinguishable, which may lead to low medicinal efficacy or poison. Therefore, the *Bupleurum* is identified by chromosomal DNA polymorphism and nucleotide sequence divergence of internal transcribed spacer (ITS) of ribosomal RNA (rRNA). Thus, *Bupleurum* according to the invention comprises the *Bupleurum* with a nucleotide sequence selected from a group consisting of: SEQ ID NOs. 1~6 and a nucleotide sequence with no more than 1% of the nucleotide sequence divergences of SEQ ID NOs. 1~6.

The *Bupleurum* can be extracted from the root of a plant or a whole plant. The "extraction" according to the invention can be solvent extraction. The "solvent extraction" is directed to a method comprising: adding a substrate of interest into a suitable solvent and extracting a target compound based on the solubility of components of the substrate in the solvent. In one example, the *Bupleurum* is ground and immerged in a solvent under room temperature for a period of time. The solvent is isolated and dried under room temperature to obtain an extract of the *Bupleurum*. In another example, the ground *Bupleurum* is added into a polar solvent and extracted after heating under reflux.

The solvent used in the invention can be $C_1$~$C_{12}$ alcohols, $C_2$~$C_5$ acetates, $C_5$~$C_6$ alkanes, or combinations thereof, such as methanol, ethanol, propanol, isopropanol, butanol, 2-butyl alcohol, tert-butyl alcohol, 1,3-butandiol, 1,4butandiol, pentanol, isopentanol, 2,3-pentandiol, 2,4-pentandiol, cyclopentanol, hexanol, cyclohexanol, heptanol, octanol, nonanol, decanol, undecanol, dodecanol, ethyl acetate, propyl acetate, pentyl acetate, pentane, cyclopentane, hexane, cyclohexane, or combinations thereof, but are not limited thereto. In one example, the invention uses ethanol, ethyl acetate and/or pentane as a solvent for extraction. In another example, the invention uses an ethanol aqueous solution as a solvent for extraction. The concentration of ethanol can be 20%~95%, preferably 50%~75% based on the ethanol aqueous solution.

The volume of the solvent can be more than 5 times that of the *Bupleurum*, or preferably 5~10 times.

The extraction is usually more than 2 hours, preferably 2~24 hours, more preferably 4~5 hours.

The extraction is usually under room temperature, preferably under room temperature to the boiling temperature of the ethanol aqueous solution, more preferably under the boiling temperature of the ethanol aqueous solution.

The extraction can further comprise a concentration process to concentrate and dry the extract after heating under reflux, wherein a solid or crystal is obtained. The extraction can be repeated several times to obtain a pure extract.

The extract of *Bupleurum* according to the invention shows activities for inhibiting the expression of TNF-α or IL-6 in vivo, as shown in following examples, exhibiting immunomodulating function.

The extract of *Bupleurum* according to the invention can be further isolated, such as by recrystallization. Kaerophyllin and cis-isomer have been isolated from *Bupleurum*. Kaerophyllin is known as one of the lignins, which is trans-(3,4-dimethoxybenzylidene)-β-(3,4-methylenedioxylbenzyl)-γ-butyrolactone, $C_{22}H_{22}O_7$, as presented in the formula (1). Kaerophyllin usually forms transparent needle-like crystals at room temperature and has a melting point of 131° C.~132° C.

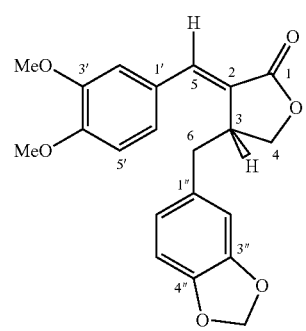

Formula (1)

The extraction and identification of kaerophyllin from *Bupleurum* has been described in publications, such as Dou H S, et al (2000) Studies on method for the determination of kaerophyllin in *Bupleurum smithii* wolff Wolff var. *parvifolium*, China Journal of Chinese Materia Medica. 2000 August; 25(8):488-9; Shang-Ming Yuan, et al (2000) Analysis of kaerophyllin in 4 kinds of Saiko by HPLC, *Northwest Pharmaceutical Journal*. 2000 15(04); Estevez-Braun A. et al., 1994, antibiotic activity and absolute configuration of 8S-Heptadeca-2(Z),9(Z)-diene-4,6-diyne-1,8-diol from *Bupleurum salicifolium*, *J. Natural Products*, 57, 1178-1182; and Estevez-Braun A. et al., 1995, Busaliol and Busalicifol, two new tetrahydrofuran lignans from *Bupleurum salicifolium*, *J. Natural Products*, 58, 887-892.

It has been discovered that kaerophyllin often exists in a mixture with cis-isomer. The cis-isomer of kaerophyllin is a transparent square crystal with a melting point of 146.5° C.~148° C., which is cis-(3,4-dimethoxybenzylidene)-β-(3, 4-methylenedioxylbenzyl)-γ-butyrolactone, $C_{22}H_{22}O_7$, as presented in the formula (2).

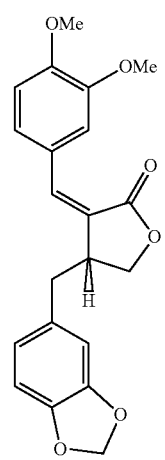

Formula (2)

Currently, there is no references to prove that kaerophyllin and cis-isomer have biological functions. However, in the following examples, kaerophyllin and the cis-isomer show an effect on the expression of TNF-α or IL-6 in vivo. Therefore, kaerophyllin and the cis-isomer have an immunomodulating function in vivo.

Therefore, according to the embodiment of invention, the pharmaceutical composition with an immunomodulation can be applied for treating, alleviating or preventing disorders or symptoms relating to the function of TNF-α or IL-6, such as septic shock, sepsis, ischemic reperfusion, mycobacterial infection, meningitis, psoriasis, congestive heart failure, cachexia, transplant rejection, cutaneous T-cell lymphoma, angiogenesis, autoimmune disorders, dermatitis, Crohn's disease, colitis, osteoarthritis and rheumatoid arthritis, ankylosing spondylitis, psoriatic arthritis, adult Still's disease, uveitis, Wegener's granulomatosis, Behcehe disease, Sjogren's syndrome, sarcoidosis, polymyositis, dermatomyositis, multiple sclerosis, sciatica, periodontal disease, adult immunodeficiency syndrome, non-insulin-dependent diabetes mellitus (NIDDM), systematic lupus erythematosus (SLE), glaucoma, idiopathic pulmonary fibrosis (IPF), bronchopulmonary dysplasia, retinopathy, systematic sclerosis, osteoporosis, renal ischemia, myocardial infarction, stroke, ischemic stroke, nephritis, hepatitis, glomerulonephritis, atopic dermatitis, vasculitis, allergy, seasonal allergic rhinitis, reversible airway obstruction, adult respiratory distress syndrome, asthma, chronic obstructive pulmonary disease (COPD), bronchitis, or combinations thereof, but are not limited thereto.

The pharmaceutical composition according to the embodiment of invention may further comprise pharmaceutical acceptable carriers and/or additives in an appropriate percentage, which is well known in the art.

The pharmaceutical composition can be administered intravenously, intramuscularly, orally or subcutaneously, and preferably orally. The administration can be performed in multiple dosages over a period of time. The regime can be designed according to pharmaceutical tests.

EXAMPLE 1

HPLC Analysis of *Bupleurum*

The roots of several *Bupleurum* species were ground. 0.5 g portions of the ground *Bupleurum* were individually added to 25 mL of a 95% ethanol aqueous solution and vibrated overnight. After concentrated and dried, 95% of ethanol solution was added to make a final volume of 2 mL. The solution was analyzed under high pressure liquid chromatography (HPLC) analysis.

HPLC Analysis:
Column: SymmetryShield™ (Waters), $^{RP}$18, 5 μm, 250×4.6 mmID
Mobile phase: A: $H_2O$, B: acetonitrile, C: methanol.
Detection: UV/λ=237 nm.

The HPLC chromatogram with the peak of kaerophyllin (standard, Line (a) in FIG. 1) was selected, wherein Line (b) is from a *Bupleurum* with a nucleotide sequence of SEQ ID NO. 1 (the sequencing is described in Example 18), Line (c) is from *Bupleurum* krlovianum with a nucleotide sequence of SEQ ID NO. 2, Line (d) is from *Bupleurum* longiradiatum with a nucleotide sequence of SEQ ID NO. 3, Line (e) is from *Bupleurum* with a nucleotide sequence of SEQ ID NO. 4, Line (f) is from *Bupleurum* with a nucleotide sequence of SEQ ID NO. 5, and Line (g) is from *Bupleurum* with a nucleotide sequence of SEQ ID NO. 6.

EXAMPLE 2

Extraction of *Bupleurum krlovianum*

Figure 2:
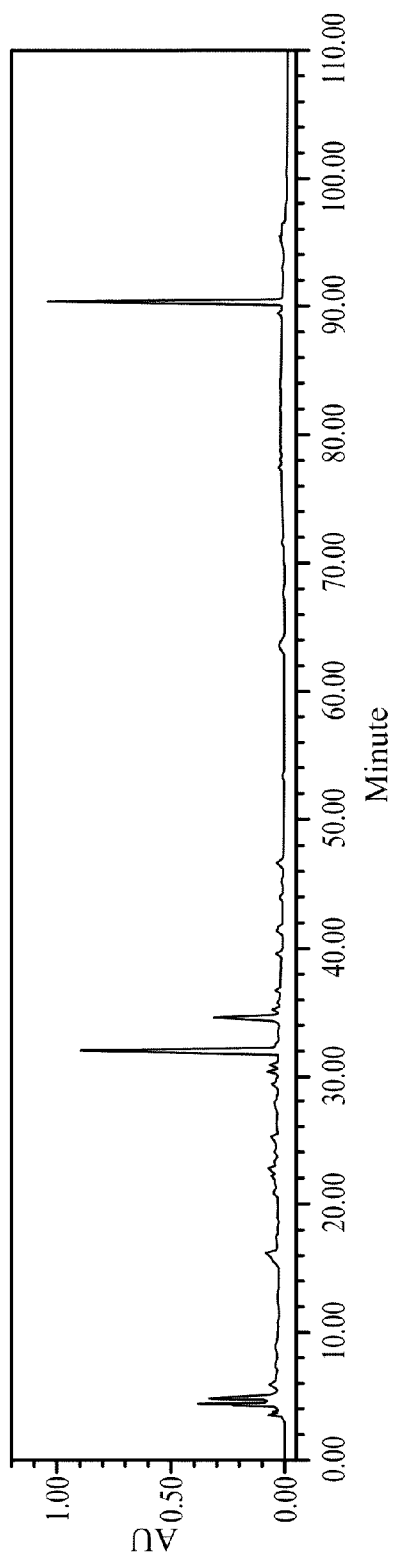
FIG. 2 is an HPLC chromatogram of the extract of *Bupleurum krlovianum* by a 95% ethanol aqueous solution.

2 kg of the ground *Bupleurum krlovianum* selected in Example 1 was added into 16 L of a 95% ethanol aqueous solution. After 5 hours at room temperature, the solution was concentrated to obtain an extract with a 6.7±0.1% extraction yield. The extract was then analyzed under HPLC analysis. The resulting chromatogram shows peaks between 30-40 minutes (FIG. 2).

HPLC Analysis:
Column: SymmetryShield™ (Waters), $^{RP}$18, 5 μm, 250×4.6 mmID
Mobile phase: A: $H_2O$, B: acetonitrile, C: methanol.
Detection: UV/λ=237 nm.

EXAMPLE 3

Identification of Active Ingredients 18.5 kg of the ground *Bupleurum krlovianum* selected in Example 1 was added into 25 L of methanol. After 4 hours under room temperature, the solution was dried and concentrated to obtain 18.5 kg of residues. 500 mg of the residues was purified by using column chromatography (stationary phase: $SiO_2$, mobile phase: hexane, ethyl acetate and methanol with ratio of 6/4/1, 3/2/1 and 0/0/1) and elutes were collected separately. Each elutes was fractionated by thin layer chromatography (TLC) and 12 fractions were collected, respectively. Each of the 12 fractions was added to methanol to make a final concentration of 1 mg/ml and analyzed by the HPLC analysis of Example 1. A chromatogram with the peak of kaerophyllin (standard) was selected. The selected fraction was further purified by the column chromatography and an extract with higher purity was isolated. The extract was further crystallized to obtain white transparent crystals (1).

Figure 3A:
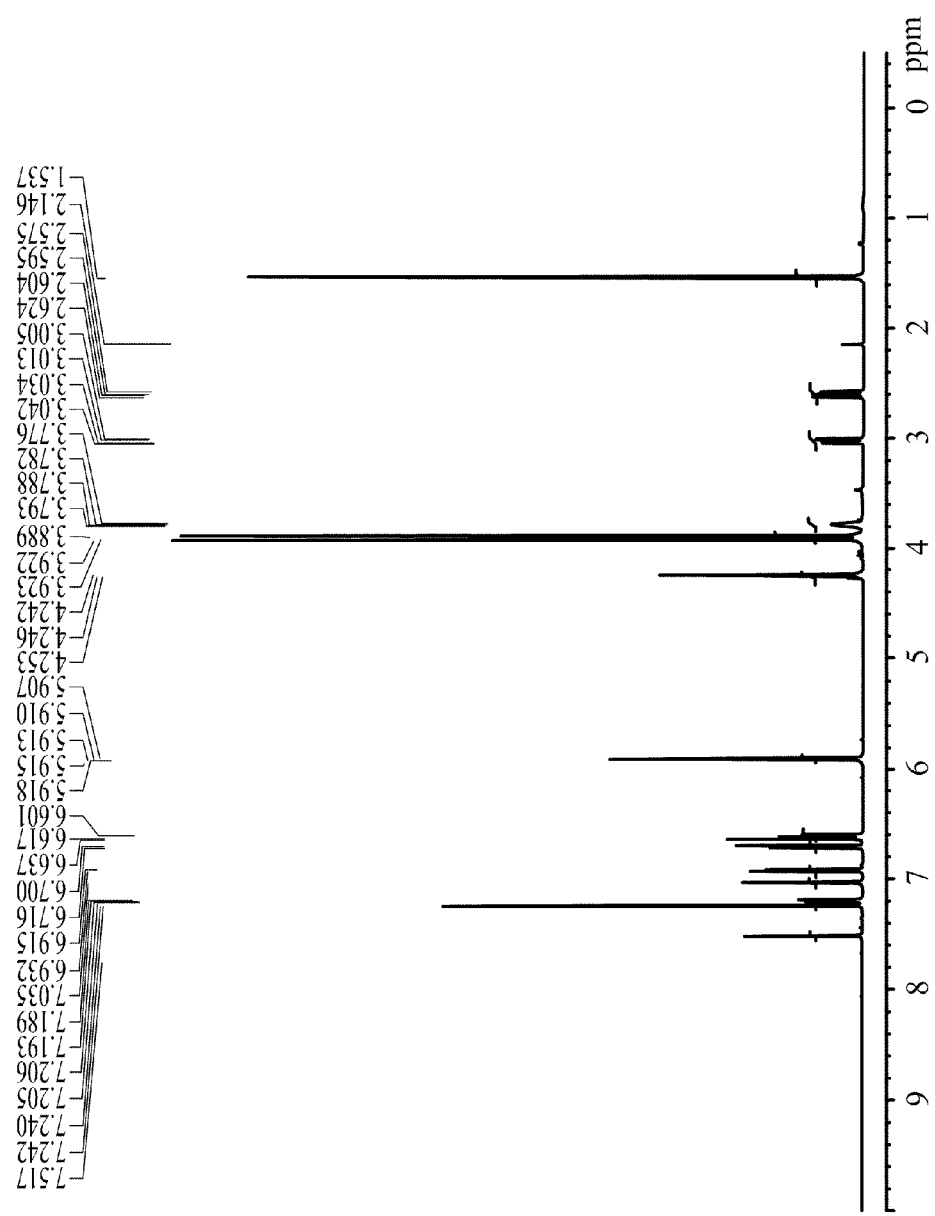
FIG. 3a is a $^1$H NMR spectrum of the crystal (1) in Example 3.

The crystal (1) was studied by $^1$H-NMR, $^{13}$C-NMR and MS spectroscopy. As the result in Table 1, Table 2 and FIG. 3a shows, there were chemical shifts at 6-8 ppm and 2.5-4 ppm, suggesting that there were $C_3$ and $C_6$ lignins. Comparing the information of the kaerophyllin described in Wen-Liang C. et al., 2003, Immunosuppressive flavones and lignans from *Bupleurum scorzonerifolium*, Phytochemistry 64, 1375-1379, the crystal (1) were identified as kaerophyllin.

TABLE 1

$^1$H-NMR data of kaerophyllin in Wen-Liang C. et al. and the crystal (1) of Example 3

| Location | δH mult of kaerophyllin in Wen-Liang C. et al. | δH mult of the crystal (1) of Example 3 |
|---|---|---|
| 3 | 3.78m | 3.78 |
| 4α | 4.24m | 4.24 |
| 4β | 4.24m | 4.24 |
| 5 | 7.50s | 7.51 |
| 6α | 2.58dd(14.4, 10.3) | 2.59 |
| 6β | 3.01dd(14.4, 4.1) | 3.01 |
| 2' | 7.02d(1.5) | 7.03 |
| 5' | 6.91d(8.4) | 6.91 |
| 6' | 7.19dd(8.4, 1.5) | 7.19 |
| 2" | 6.62d(1.5) | 6.61 |
| 5" | 6.69d(7.8) | 6.67 |
| 6" | 6.59dd(7.8, 1.5) | 6.60 |
| 3'-OMe | 3.88s | 3.88 |
| 4'-OMe | 3.91s | 3.92 |
| $OCH_2O$ | 5.90d(1.5) | 5.90 |

TABLE 2

¹³C-NMR (CDCl₃) data of kaerophyllin in Wen-Liang
C. et al. and the crystal (1) of Example 3

| Location | δC of kaerophyllin in Wen-Liang C. et al. | δC of the crystal (1) of Example 3 |
|---|---|---|
| 1 | 172.56 | 172.57 |
| 2 | 125.58 | 125.73 |
| 3 | 39.60 | 39.72 |
| 4 | 69.46 | 69.53 |
| 5 | 137.39 | 137.43 |
| 6 | 37.53 | 37.50 |
| 1' | 126.82 | 126.97 |
| 2' | 112.87 | 113.06 |
| 3' | 150.65 | 150.80 |
| 4' | 149.05 | 149.21 |
| 5' | 111.25 | 111.40 |
| 6' | 123.54 | 123.54 |
| 1" | 131.43 | 131.54 |
| 2" | 108.91 | 109.06 |
| 3" | 147.91 | 148.03 |
| 4" | 146.49 | 146.61 |
| 5" | 108.41 | 108.50 |
| 6" | 121.89 | 121.97 |
| 3'-OMe | 55.93 | 56.05 |
| 4'-OMe | 55.96 | 56.05 |
| OCH₂O | 101.02 | 101.10 |

Figure 3B:
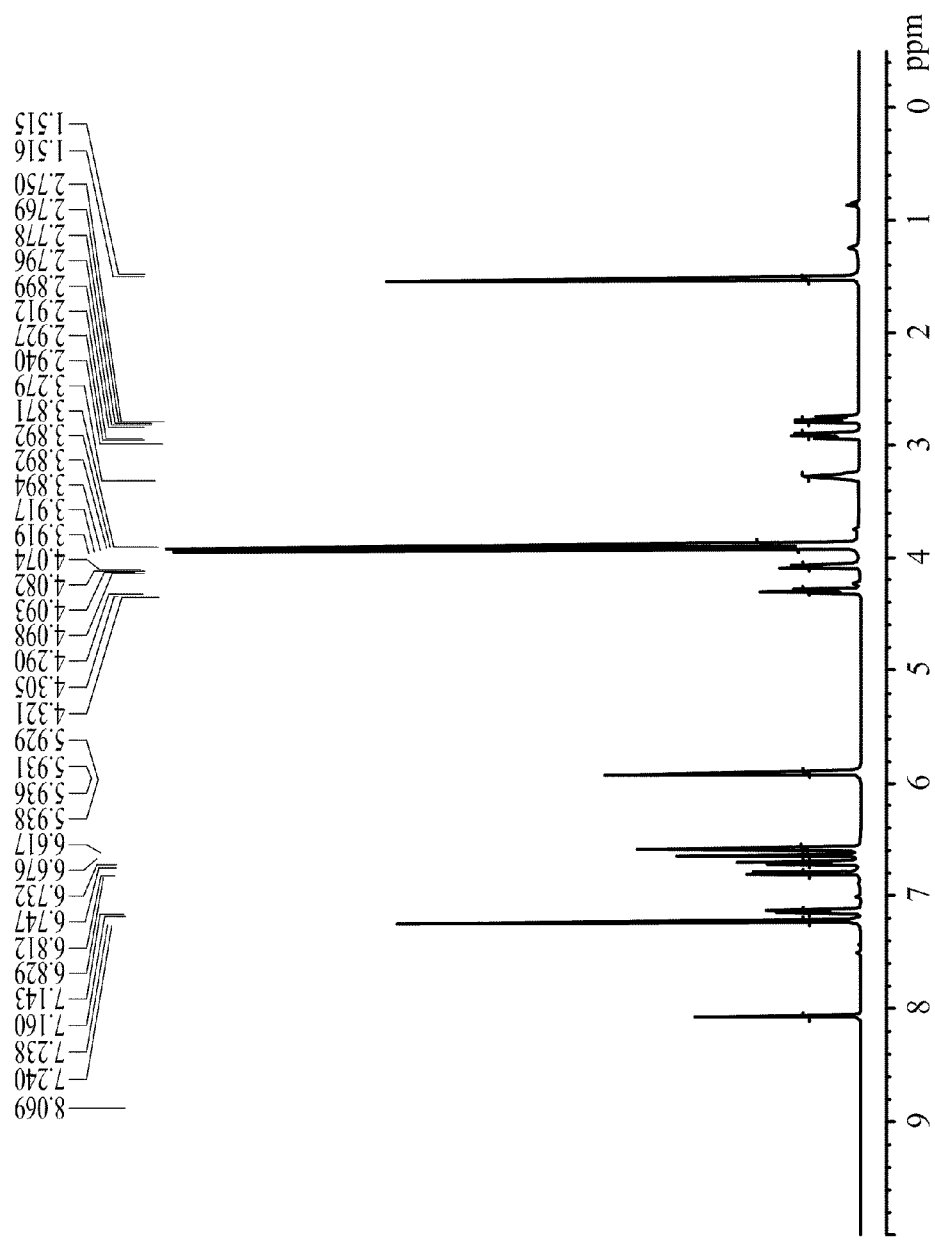
FIG. 3b shows a $^1$H NMR spectrum of the crystal (2) in Example 3.

The selected fraction in Example 3 was recrystallized in hexane to obtain transparent square crystals (2). The crystal was studied by ¹H-NMR, ¹³C-NMR and MS spectroscopy and the results are shown in Table 3, Table 4 and FIG. 3b. Comparing the information of the isokaerophyllin described in Wen-Liang C. et al., 2003, Immunosuppressive flavones and lignans from *Bupleurum scorzonerifolium*, *Phytochemistry* 64, 1375-1379, it was identified that the crystal (2) was isokaerophyllin.

TABLE 3

¹H-NMR data of isokaerophyllin in Wen-Liang
C. et al. and the crystal (2) of Example 3

| Location | δH mult of isokaerophyllin in Wen-Liang C. et al. | δH mult of the crystal (2) of Example 3 |
|---|---|---|
| 3 | 3.28m | 3.28 |
| 4α | 4.09 | 4.09 |
| 4β | 4.30m | 4.3 |
| 5 | 6.61s | 6.61 |
| 6α | 2.77dd | 2.76 |
| 6β | 2.92dd | 2.92 |
| 2' | 8.07d | 8.07 |
| 5' | 6.82d | 6.81 |
| 6' | 7.15dd | 7.14 |
| 2" | 6.68d | 6.67 |
| 5" | 6.74d | 6.74 |
| 6" | 6.62dd | 6.61 |
| 3'-OMe | 3.89s | 3.89 |
| 4'-OMe | 3.92s | 3.91 |
| OCH₂O | 5.93d | 5.93 |

TABLE 4

¹³C-NMR (CDCl₃) data of isokaerophyllin
and the crystal (2) of Example 3

| Location | δC of isokaerophyllin in Wen-Liang C. et al. | δC of the crystal (2) of Example 3 |
|---|---|---|
| 1 | 172.56 | 172.57 |
| 2 | 125.58 | 125.73 |
| 3 | 39.6 | 39.72 |
| 4 | 69.46 | 69.53 |
| 5 | 137.39 | 137.43 |
| 6 | 37.53 | 37.6 |
| 1' | 126.82 | 126.97 |
| 2' | 112.87 | 113.06 |
| 3' | 150.65 | 150.8 |
| 4' | 149.05 | 149.21 |
| 5' | 111.25 | 111.4 |
| 6' | 123.54 | 123.54 |
| 1" | 131.43 | 131.54 |
| 2" | 108.91 | 109.06 |
| 3" | 147.91 | 148.03 |
| 4" | 146.49 | 146.61 |
| 5" | 108.41 | 108.5 |
| 6" | 121.89 | 121.97 |
| 3'-OMe | 55.93 | 56.05 |
| 4'-OMe | 55.96 | 56.05 |
| OCH₂O | 101.02 | 101.1 |

The white crystal (1) and transparent square crystal (2) of Example 3 were studied under HPLC analysis, which comprised:
Column: ODS 3V,
Mobile phase: CH₃OH/H₂O (0.1% H₃PO₄), gradient elution,
Flow rate: 1.0 ml/min, and
Detection: UV/λ=310 nm.

Figure 4A:
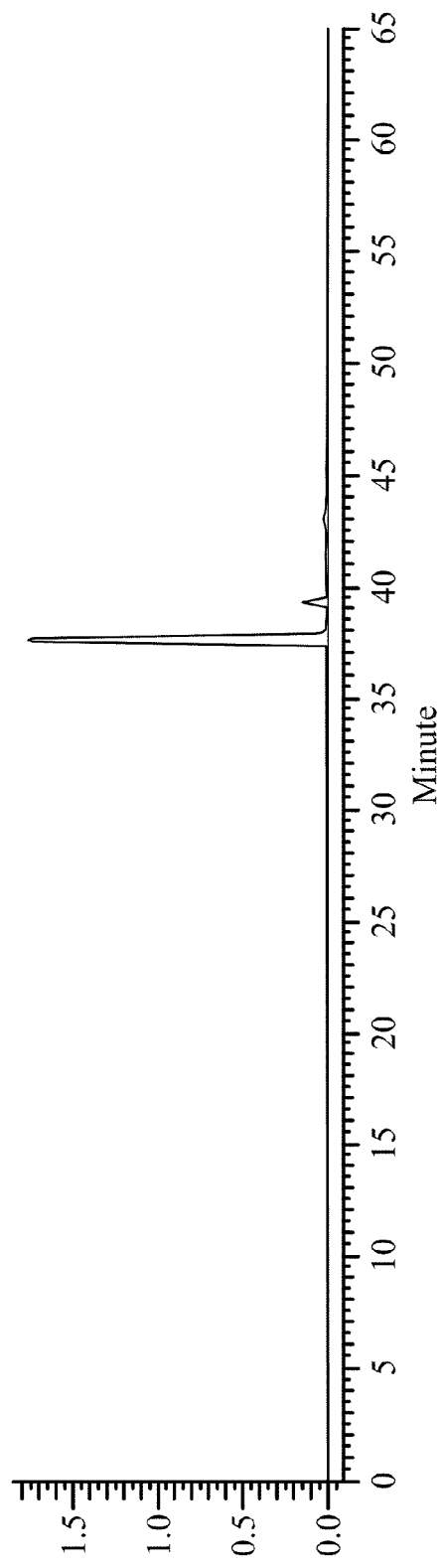
FIG. 4a is an HPLC chromatogram of kaerophyllin.
Figure 4B:
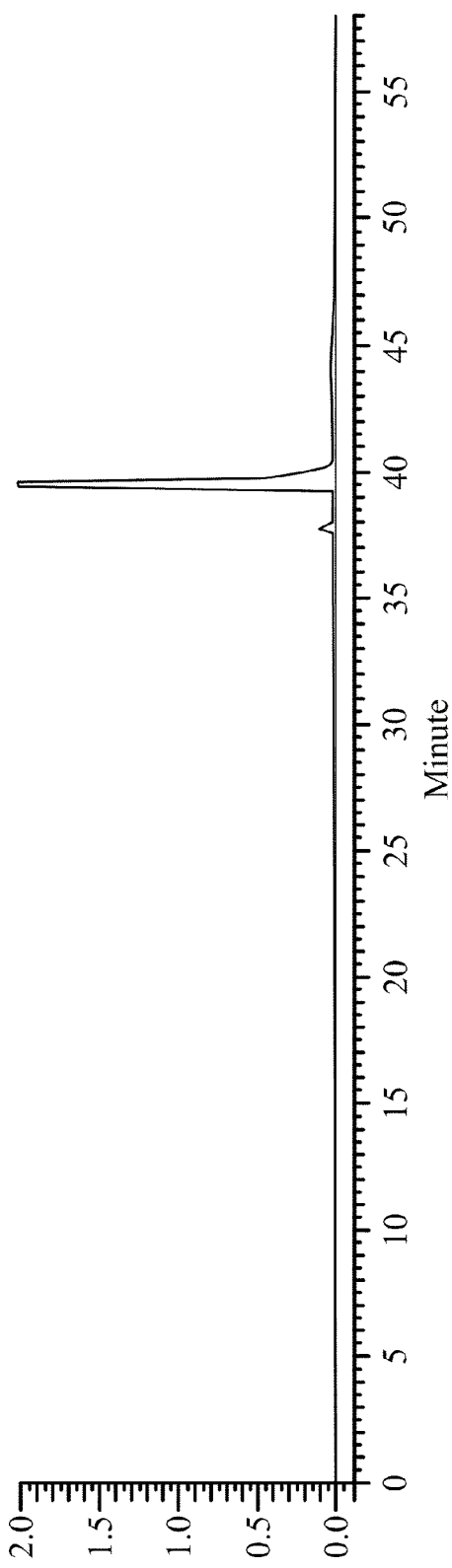
FIG. 4b shows an HPLC chromatogram of isokaerophyllin.

The resulting chromatograms showed that the white crystal (1) (kaerophyllin) had a peak at about 37 minutes (FIG. 4a) and the transparent square crystal (2) (isokaerophyllin) had a peak at about 40 minutes (FIG. 4b).

EXAMPLE 4

Inhibition of the Extracts by Different Concentrations of Ethanol Extracts 200 g of the ground *Bupleurum krlovianum* selected in Example 1 was equally divided and added to a four 1 L round bottom flask. Each flask was added ethanol aqueous solutions with 20%, 50%, 75% and 95% concentrations, individually. After heating under reflux for 2 hours, each of the solutions was dried and concentrated to obtain extracts.

BALB/c mice were fed with the extracts in an amount of 500 mg/kg, respectively. After 2 hours, the mice were intraperitoneally injected with 1 mg/kg of lipopolysaccharide (LPS) in phosphate buffered saline (PBS). Blood was collected after 1.5 hours. The concentration of TNF-α and IL-6 in the mice serum was quantified by ELISA (R&D System®). The inhibition rates (%) of TNF-α and IL-6 in the serum were calculated based on the concentration of TNF-α and IL-6 in the serum before the mice were fed with the extracts. The results are shown in Table 5.

TABLE 5

| Ethanol concentration for extraction | Inhibition of TNF-α (%) | Inhibition of IL-6 (%) |
|---|---|---|
| 25% | 57.7 | 26.2 |
| 50% | 92.8 | 81.7 |
| 75% | 92.4 | 74.0 |
| 95% | 71.4 | 40.3 |

EXAMPLE 5

Inhibition of the Extracts by Different Solvent Extractions (i) Extraction by 50% ethanol: 50 g of the ground *Bupleurum krlovianum* selected in Example 1 and 500 ml of 50% ethanol aqueous solution were added to a 1 L round bottom flask. After heating under reflux for 2 hours, the solution was dried and concentrated to obtain an extract (a). The extract (a) was used in the following in vivo experiments.

(ii) Extraction by hexane: 50 g of the ground *Bupleurum krlovianum* selected in Example 1 and 500 ml of 50% ethanol aqueous solution were added to a 1 L round bottom flask. The flask was heated under reflux for 2 hours and added 100% hexane in an equal amount of the solution in the flask. The step was repeated three times. The solution in the flask was dried and concentrated to obtain an extract (b). The extract (b) was used in the following in vivo experiments.

(iii) Extraction by ethyl acetate: 50 g of the ground *Bupleurum krlovianum* selected in Example 1 and 500 ml of 50% ethanol aqueous solution were added to a 1 L round bottom flask. The flask was heated under reflux for 2 hours and added ethyl acetate in an equal amount of the solution in the flask. The step was repeated three times. The solution in the flask was dried and concentrated to obtain an extract (c). The extract (c) was used in the following in vivo experiments.

(iv) In vivo experiments: BALB/c mice were fed with the extracts (a), (b) and (c) in an amount of 500 mg/kg, respectively. After 2 hours, the mice were intraperitoneally injected with 1 mg/kg of LPS in PBS. Blood was collected after 1.5 hours. The concentration of TNF-$\alpha$ and IL-6 in the mice serum was quantified by ELISA (R&D System®). The inhibition rates (%) of TNF-$\alpha$ and IL-6 in the serum were calculated based on the concentration of TNF-$\alpha$ and IL-6 in the serum before the mice were fed with the extracts. The results are shown in Table 6.

TABLE 6

| Solvent extraction | Extracts | Inhibition of TNF-$\alpha$ (%) | Inhibition of IL-6 (%) |
|---|---|---|---|
| 50% ethanol | (a) | 92.8 | 81.7 |
| 50% ethanol + hexane | (b) | 99.3 | 78.4 |
| 50% ethanol + ethyl acetate | (c) | 98.6 | 83.0 |

EXAMPLE 6

The Isolation of Kaerophyllin by Different Solvent Extractions 5 g of the ground *Bupleurum krlovianum* selected in Example 1 was equally divided and added to five 1 L round bottom flasks. Each flask was added 10 ml of methanol, ethanol, isopropanol, butanol and decanol, respectively. Each flask was ultrasound vibrated for 10 minutes and the extracts were collected individually. The volume for each extract was adjusted to 10 ml. Meanwhile, standards were established as follows: 0.3 mg/ml, 0.27 mg/ml, 0.21 mg/ml, 0.15, 0.09 mg/ml, 0.06 mg/ml and 0.03 mg/ml of kaerophyllin. The amounts of kaerophyllin in the extracts were determined as shown in Table 7.

TABLE 7

| Solvent for extraction | The amount of kaerophyllin in the extracts (%) |
|---|---|
| Methanol | 0.32 |
| Ethanol | 0.30 |
| Isopropanol | 0.21 |
| Butanol | 0.08 |
| Decanol | 0.10 |

EXAMPLE 7

Inhibition Effects by Different Extraction Times 2.0 kg of the ground *Bupleurum krlovianum* selected in Example 1 and 16.3 L of 50% ethanol solution were added to a 20 L round bottom flask under heating with reflux. The solutions were collected separately after 2, 3, 4 and 5 hours and then dried and concentrated to obtain extracts. Meanwhile, standards were established as follows: 0.3 mg/ml, 0.27 mg/ml, 0.21 mg/ml, 0.15, 0.09 mg/ml, 0.06 mg/ml and 0.03 mg/ml of kaerophyllin. The amounts of kaerophyllin in the extracts were determined as shown in Table 8.

In addition, BALB/c mice were fed with the extracts in an amount of 500 mg/kg, respectively. After 2 hours, the mice were intraperitoneally injected with 1 mg/kg of LPS in PBS. Blood was collected after 1.5 hours. The concentration of TNF-$\alpha$ and IL-6 in the mice serum was quantified by ELISA (R&D System®). The inhibition rates (%) of TNF-$\alpha$ and IL-6 in the serum were calculated based on the concentration of TNF-$\alpha$ and IL-6 in the serum before the mice were fed with the extracts. The results are shown in Table 8.

TABLE 8

| Extraction time | The amount of kaerophyllin in the extract | Inhibition of TNF-$\alpha$ (%) | Inhibition of IL-6 (%) |
|---|---|---|---|
| 2 hr | 1.10 | 84.4 | −34.7 |
| 3 hr | 1.08 | 70.5 | −6.8 |
| 4 hr | 1.06 | 100.0 | 46.0 |
| 5 hr | 1.06 | 99.7 | −0.9 |

EXAMPLE 8

Figure 5:
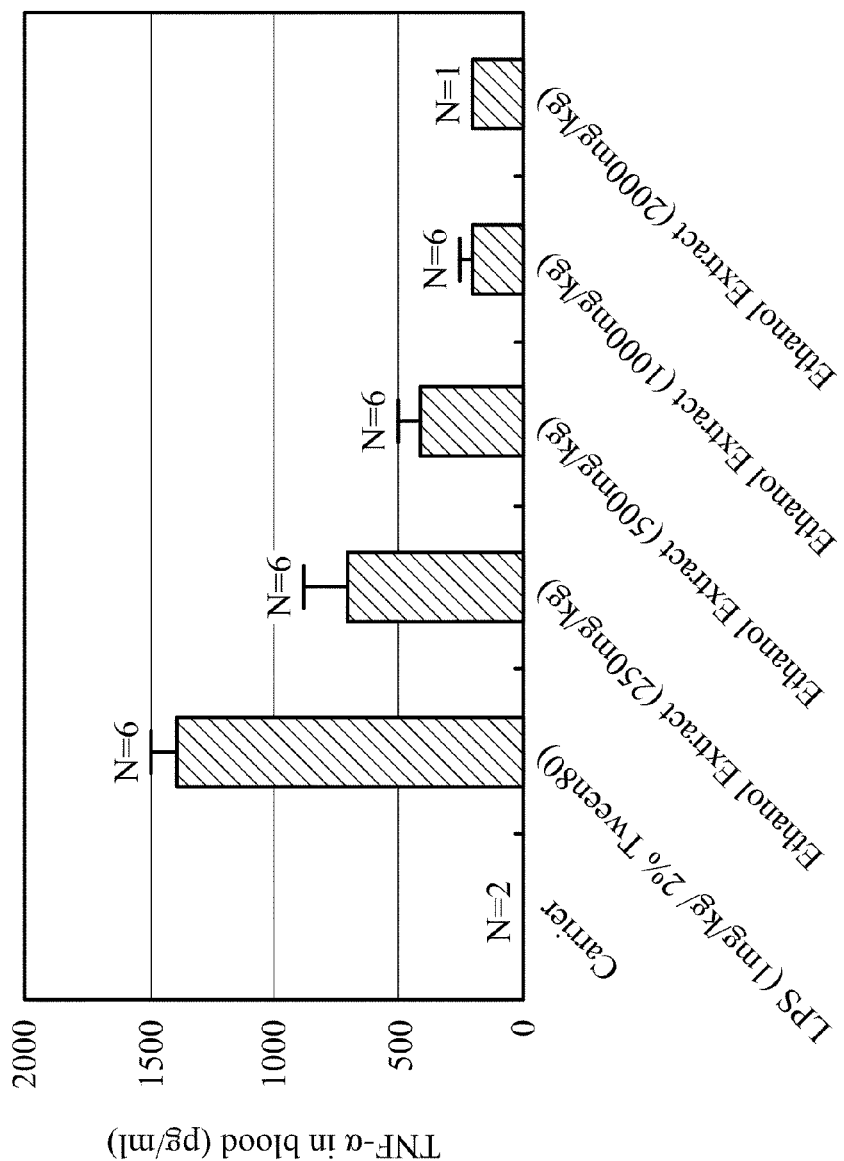
FIG. 5 is the inhibition of TNF-$\alpha$ in an LPS-induced inflammatory animal model by different amounts of the ethanol extract of *Bupleurum*.
Figure 6:
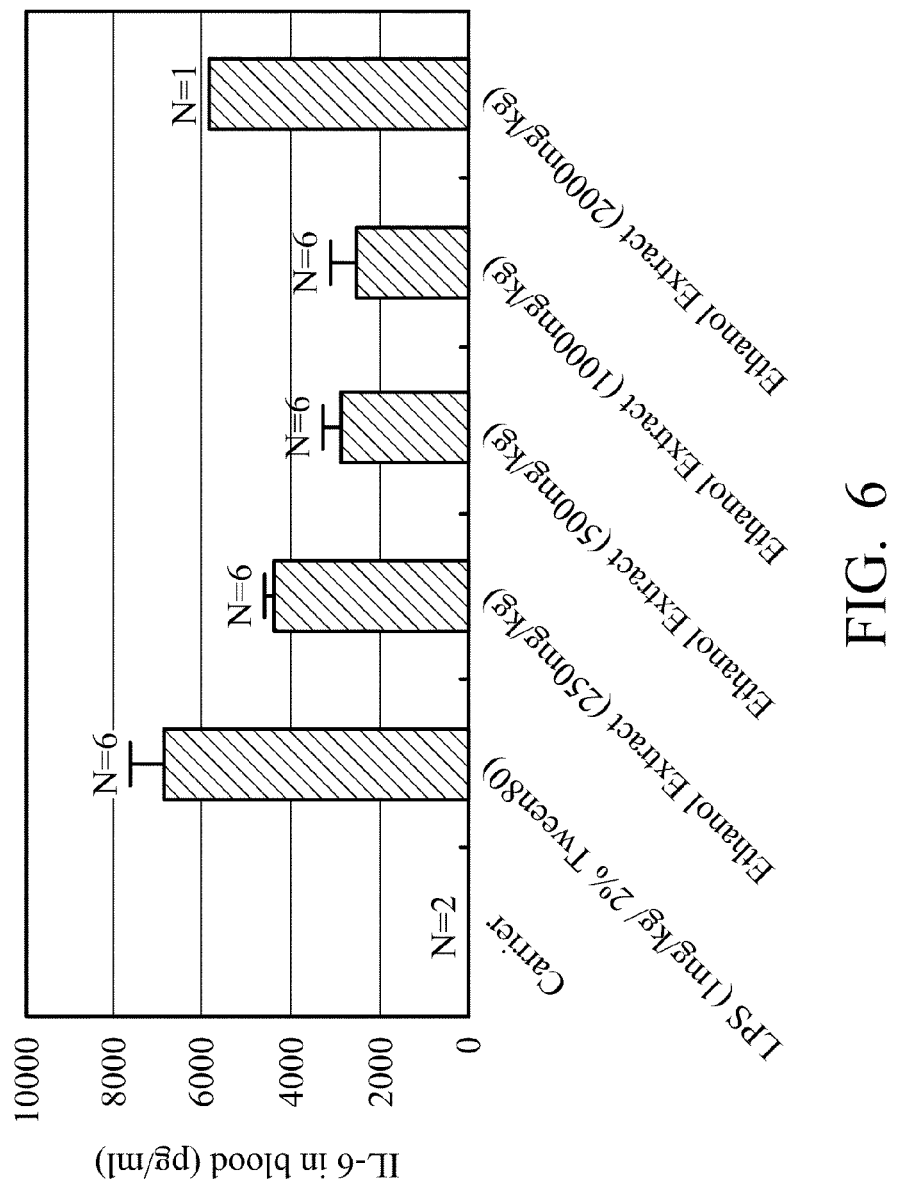
FIG. 6 is the inhibition of IL-6 in an LPS-induced inflammatory animal model by the amounts of the ethanol extract of *Bupleurum*.
Figure 7:
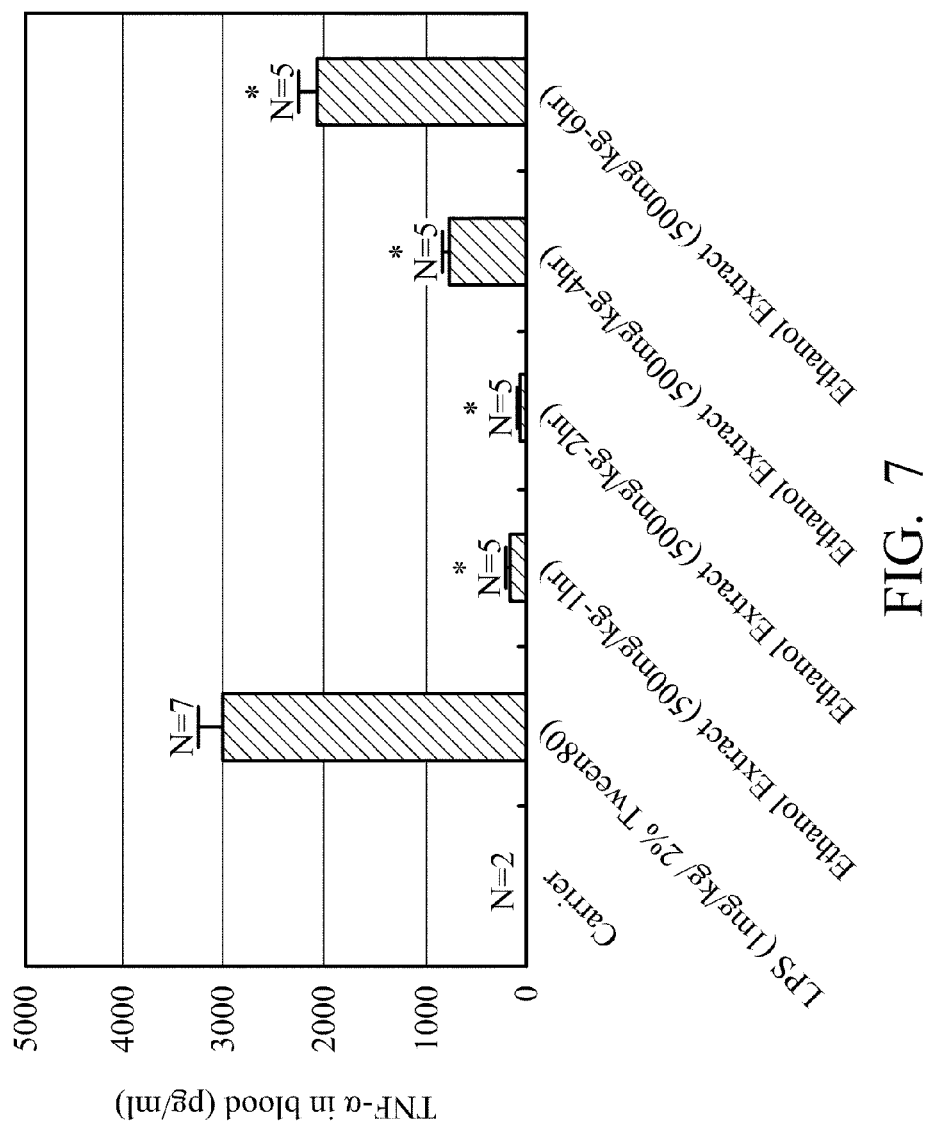
FIG. 7 is the inhibition of TNF-$\alpha$ in an LPS-induced inflammatory animal model by the ethanol extract of *Bupleurum* overtimes.
Figure 8:
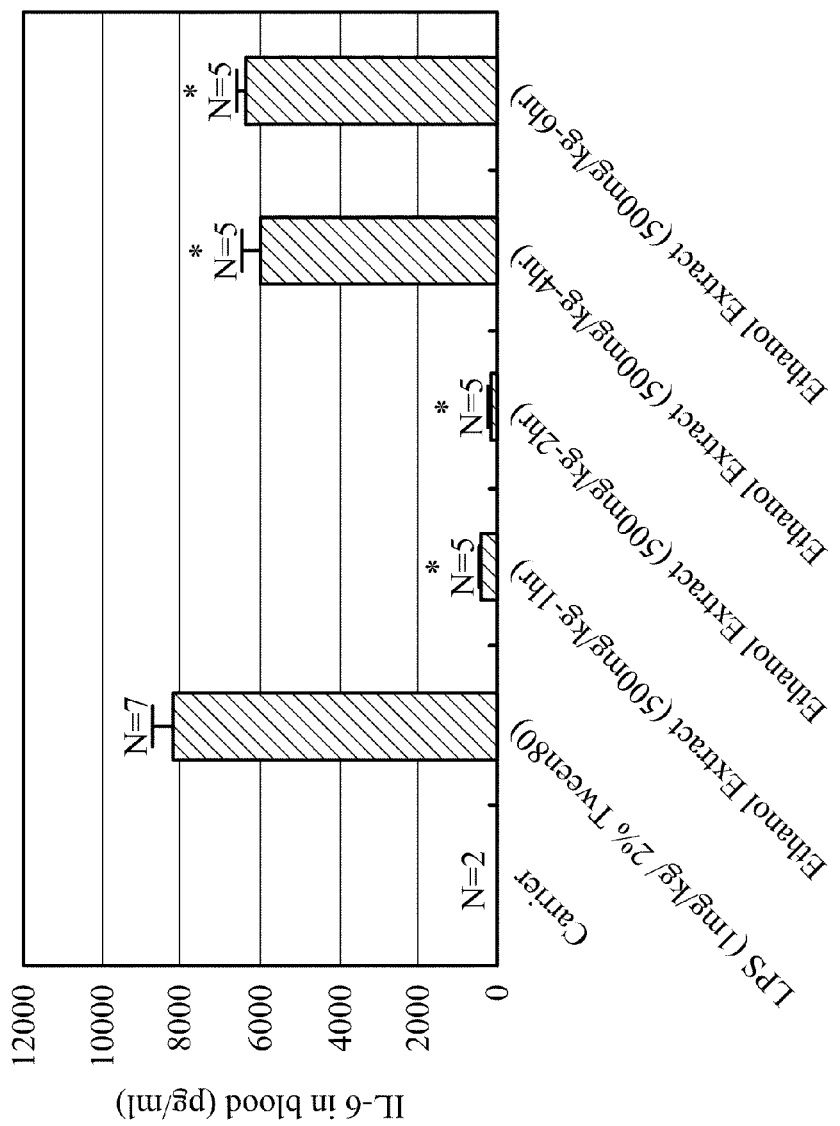
FIG. 8 is the inhibition of IL-6 in an LPS-induced inflammatory animal model by the ethanol extract of *Bupleurum* overtimes.
Figure 9:
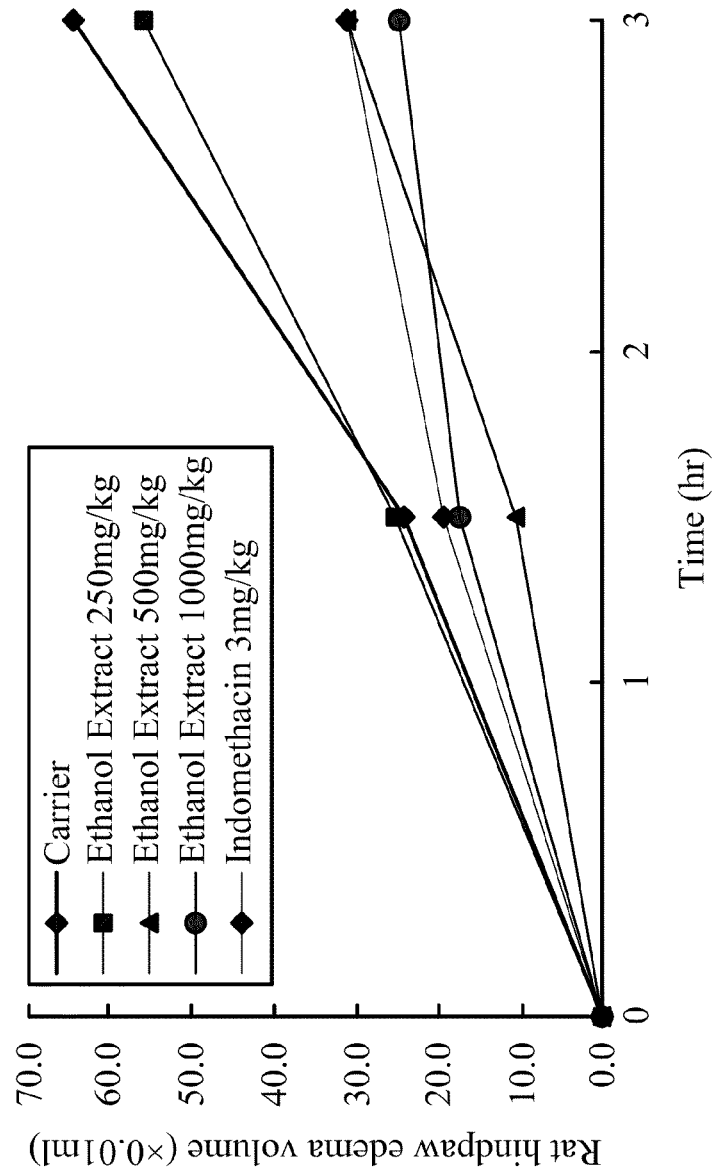
FIG. 9 is the inhibition of hindpaw edema in a carrageenan-induced hindpaw edema animal model by the ethanol extract of *Bupleurum*.

Effect of the Ethanol Extract on LPS-Induced Inflammatory Response in a Mouse Model BALB/c mice were fed with the extract (a) in Example 5 (i) in an amount of 250 mg/kg, 500 mg/kg, 1000 mg/kg and 2000 mg/kg, respectively. After 2 hours, the mice were intraperitoneally injected with 1 mg/kg of LPS in PBS. Blood was collected after 1.5 hours. The concentration of TNF-$\alpha$ and IL-6 in the mice serum was quantified by ELISA (R&D System®). The inhibition rates (%) of TNF-$\alpha$ and IL-6 in the serum were calculated based on the concentration of TNF-$\alpha$ and IL-6 in the serum before the mice were fed with the extracts. The results are shown in FIGS. 5 and 6. The control was fed with 10 ml/kg of 2% Tween 80 as a carrier.

EXAMPLE 9

Effect of the Ethanol Extract on LPS-Induced Inflammatory Response in a Mouse Model at Different Administration Times BALB/c mice were fed with the extract (a) in Example 5 (i) in an amount of 500 mg/kg. The mice were intraperitoneally injected with 1 mg/kg of LPS in PBS respectively at 1, 2, 4 and 6 hours after being fed with the extract. Blood was collected after 1.5 hours. The concentration of TNF-α and IL-6 in the mice serum was quantified by ELISA (R&D System®). The inhibition rates (%) of TNF-α and IL-6 in the serum were calculated based on the concentration of TNF-α and IL-6 in the serum before the mice were fed with the extract. The results are shown in FIGS. 5 and 6. The control was fed with 10 ml/kg of 2% Tween 80 as a carrier.

EXAMPLE 10

Effect of the Ethanol Extract on Carrageenan Induced Hindpaw Edema in a Rat Model Long-Evan rats were fed with the extract (a) in Example 5 (i) in an amount of 250 mg/kg, 500 mg/kg, 1000 mg/kg, respectively. The positive control was fed with 3 mg/kg of indomethacin (NSAID). The negative control was fed with 10 ml/kg of 2% Tween 80 as a carrier. After 1 hour, the rats were injected 0.1 ml of 1% carrageenan on the left hindpaw. The volume of the rat's left hindpaw was measured by plethysmometer (Stoelting) at the 0, 1.5th, and 3rd hour after injection. The inhibition was calculated by the formula:

Inhibition(%)=$(Nt-Nv)/Nv \times 100$

In the formula, Nt represents the left hindpaw volume of the rat fed with the ethanol extract; Nv represents the left hindpaw of the rat fed with the carrier.

The inhibition was negative when the ethanol extract showed anti-inflammatory effects.

TABLE 9

| Administration | Inhibition at 0 hour (%) | Inhibition at the 1.5th hour (%) | Inhibition at the 3rd hour (%) |
|---|---|---|---|
| Carrier | 0 | 0 | 0 |
| 250 mg/kg of ethanol extract | 0 | 3 | 14 |
| 500 mg/kg of ethanol extract | 0 | 55 | 52 |
| 1000 mg/kg of ethanol extract | 0 | 29 | 62 |
| 3 mg/kg of indomethacin | 0 | 21 | 52 |

EXAMPLE 11

Effect of the Ethanol Extract on Adjuvant Induced Arthritis in a Rat Model

Figure 10:
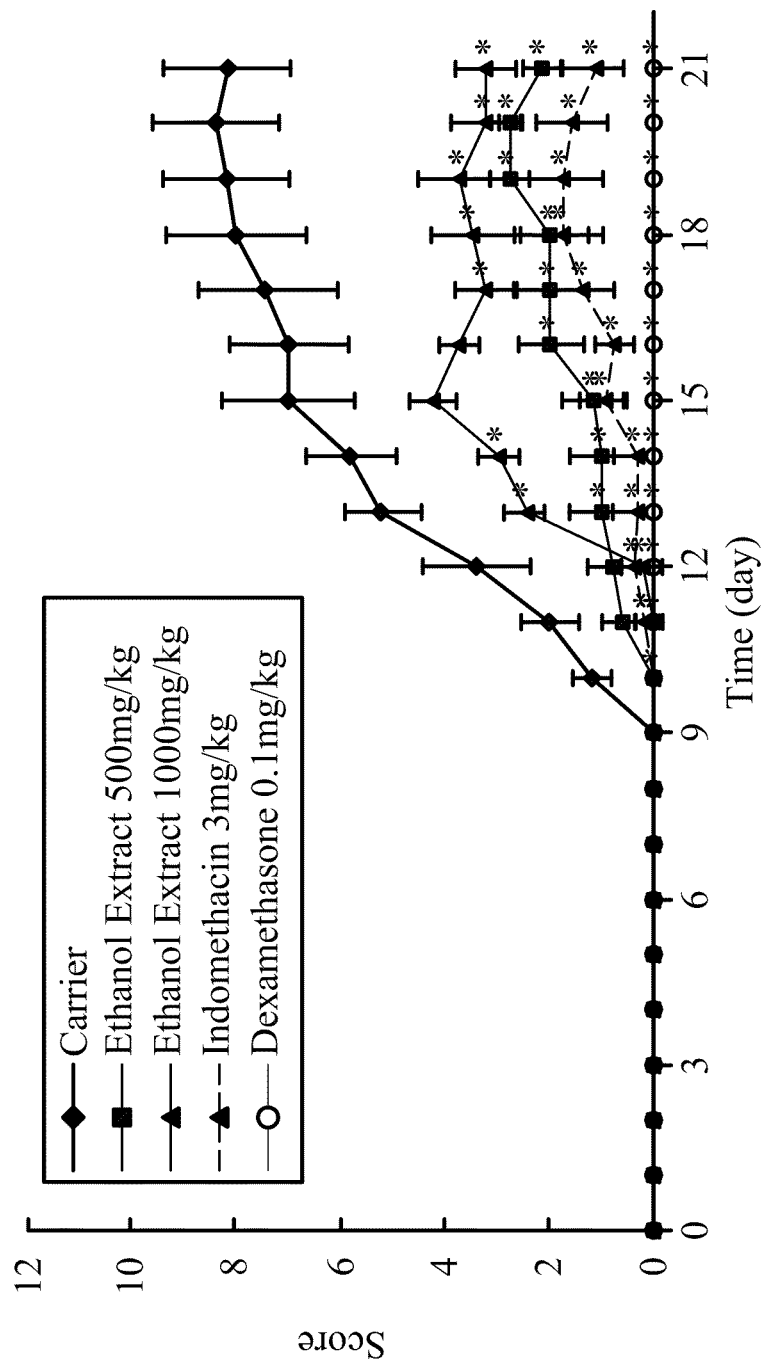
FIG. 10 is the inhibition of arthritis in an adjuvant-induced arthritis animal model by the ethanol extract of *Bupleurum*.

The rats were categorized into 5 groups. Each group had 5 rats. The rats were injected 50 μl of *Mycobacterium butyricum* in squalene at 3 points on the root of the tail (total injection: 50 μl/rat). The rats in 5 groups were immediately fed with 500 mg/kg of the extract (a) in Example 5 (i), 1000 mg/kg of the extract (a) in Example 5 (i), 3 mg/kg of indomethacin, 0.1 mg/kg of dexamethasone and 10 ml/kg of 2% Tween 80 (carrier), respectively. The symptoms of the arthritis in each group were estimated according to the scores:
  0: The feet were not red and swelling;
  1: The feet were slightly red and swelling or one toe joint was red and swelling;
  2: The feet were apparently red and swelling or more than two toe joints were red and swelling;
  3: The hindpaw was incapable of function for walking;
  4: The ankle joint was incapable of moving.
The result is shown in FIG. 10. The ethanol extract showed inhibition of arthritis, compared to the carrier group (p<0.05). The administration of indomethacin and doxamethasone was the positive control.

EXAMPLE 12

Figure 11:
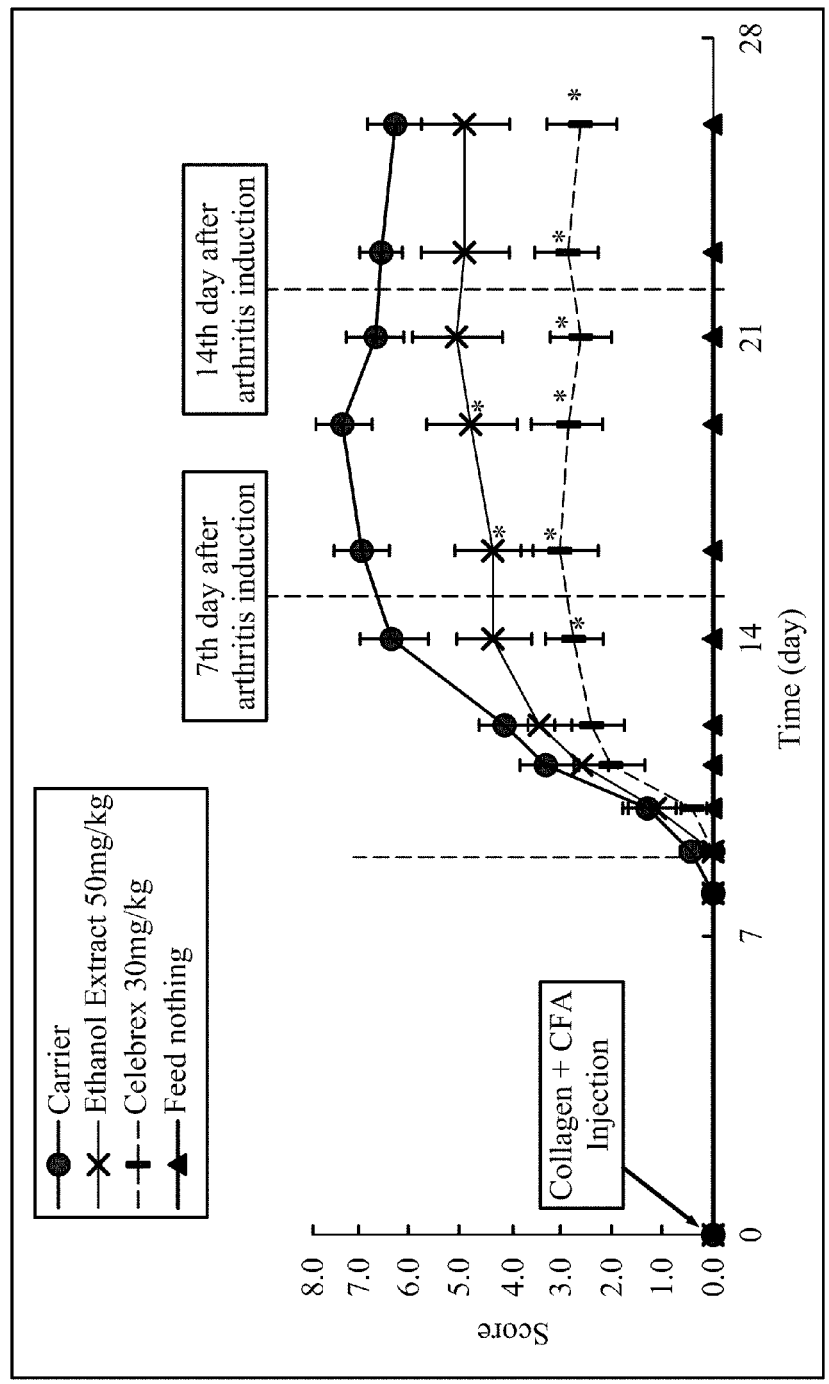
FIG. 11 is the inhibition of arthritis in an collagen-induced arthritis animal model by the ethanol extract of *Bupleurum*.

Effect of the Ethanol Extract on Collagen Induced Arthritis in a Rat Model 2 mg/ml of a fetus bovine type II collagen was emulsified with an equal amount of a complete Freund's adjuvant (CFA) or incomplete Freund's adjuvant (IFA) by homogenization (IKA, RW20 DZM.n.). The rats were categorized into 4 groups. Each group had 8 rats. Each rat was intracutaneously injected 50 μg of the collagen and CFA emulsion. At the eighth day, each rat was injected 100 μg of the collagen and IFA emulsion to induce arthritis. The rats in 4 groups were immediately fed with 50 mg/kg of the extract (a) in Example 5 (i), 30 mg/kg of celebrex (NSNID), 10 ml/kg of 1% carboxymethyl cellulose (CMC) (carrier) and nothing, respectively. The symptoms of the arthritis in each group were estimated according to the scores:
  0: The foot was not red and swelling;
  1: The foot was slightly red and swelling or one toe joint was red and swelling;
  2: The foot was apparently red and swelling or more than two toe joints were red and swelling;
  3: The hindpaw was incapable of function for walking;
  4: The ankle joint was incapable of moving.
The result showed that 50 mg/kg of the ethanol extract can cause apparent inhibition of arthritis (FIG. 11). The administration of celebrex was the positive control, and CMC was the negative control. The group fed nothing was a blank test.

EXAMPLE 13

Effect of Kaerophyllin and the Cis-Isomer on TNF-α

The cell line, U937 (human monocyte cell line), was incubated in RPMI medium containing 50 ng/ml PMA (phorbol 12-myristate 13-acetate) (Sigma) and 10% fetal bovine serum (Moor et. al., Roswell Park Memorial Institute) for 24 hours. The cell line was then moved to the RPMI medium without PMA for further 48 hours. The activated U937 was seeded into a 96-well plate in a concentration of $1.6 \times 10^5$ cell/well. The wells were added 12.5 μg/ml, 25 μg/ml, 50 μg/ml and 100 μg/ml of kaerophyllin and 1 μg/ml, 3 μg/ml, 10 μg/ml and 30 μg/ml of isokaerphyllin and 10 μl of buffer, respectively. Each well was adjusted to a final volume of 190 μl. The plate was reacted under 37° C. for 30 minutes. Each well was added 10 μl of 20 μg/ml LPS to stimulate cells. After 4 hours under 37° C., the plate was centrifuged to collect the supernatants.

The amount of TNF-α in the supernatant was measured by ELISA (R&D System®) based on the control (DMSO). Meanwhile, the cell viability was measured by MTT assay (Sigma).

Figure 12:
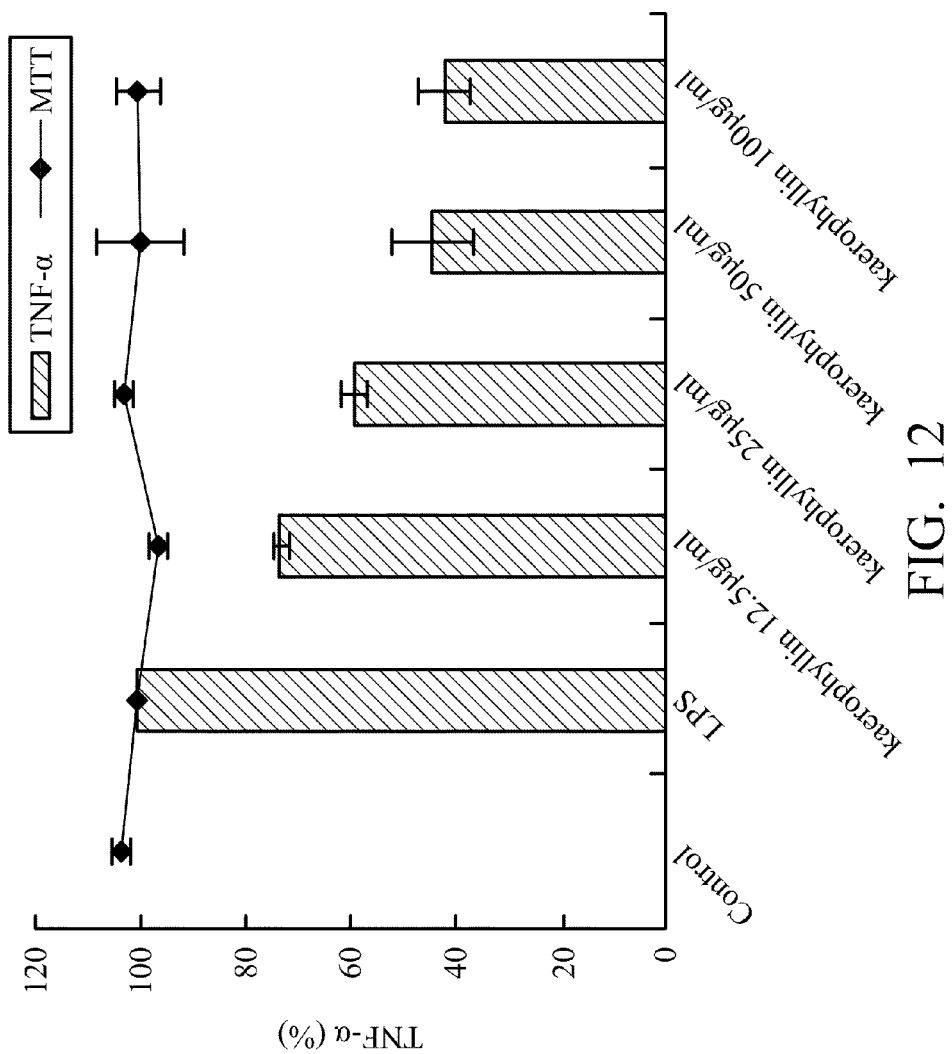
FIG. 12 is the inhibition of TNF-$\alpha$ in a U937 cell line by kaerophyllin.
Figure 13:
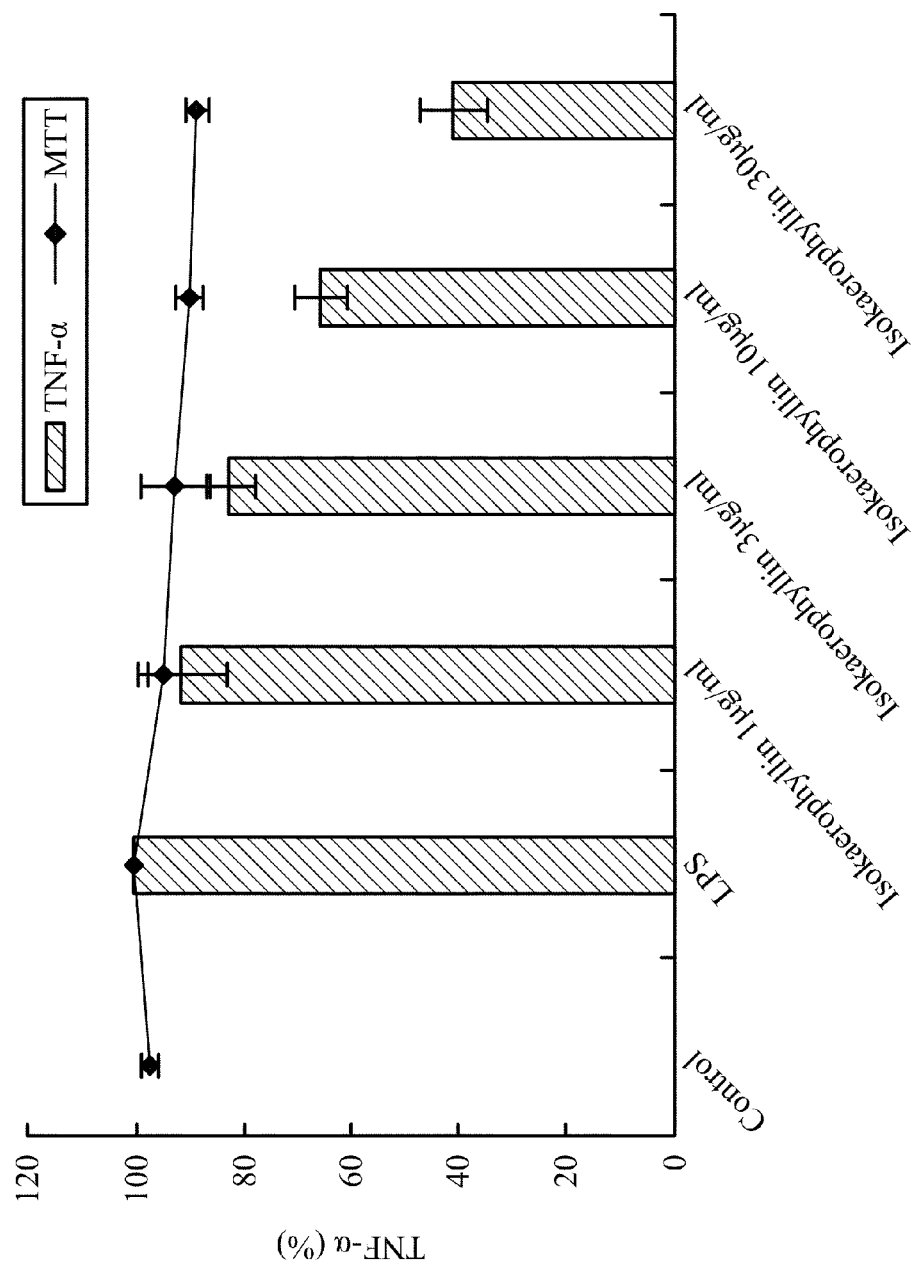
FIG. 13 is the inhibition of TNF-$\alpha$ in a U937 cell line by isokaerophyllin.

The results showed that kaerophyllin and the cis-isomer had effects to inhibit the excretion of TNF-α. The $IC_{50}$ value of kaerophyllin was 44±5 μg/ml (FIG. 12). The $IC_{50}$ value of isokaerophyllin was 18±4 μg/ml (FIG. 13).

EXAMPLE 14

Effect of Kaerophyllin and the Cis-Isomer on IL-6

The cell line, U937, was cultured like Example 13. The activated U937 was then seeded in a 96-well plate in a concentration of $1.6 \times 10^5$ cell/well. The wells were added 6.3 μg/ml, 12.5 μg/ml, 25 μg/ml and 50 μg/ml of kaerophyllin and 3.8 μg/ml, 7.5 μg/ml, 15 μg/ml and 30 μg/ml of isokaerphyllin and 10 μl of buffer, respectively. Each well was adjusted to a final volume of 190 μl. The plate was put under 37° C. for 30 minutes. Each well was added 10 μl of 20 μg/ml LPS to stimulate cells. After 16-18 hours under 37° C., the plate was centrifuged to collect the supernatants.

The amount of IL-6 in the supernatant was measured by ELISA (R&D System®) based on the control (DMSO). Meanwhile, the cell viability was measured by MTT assay (Sigma).

Figure 14:
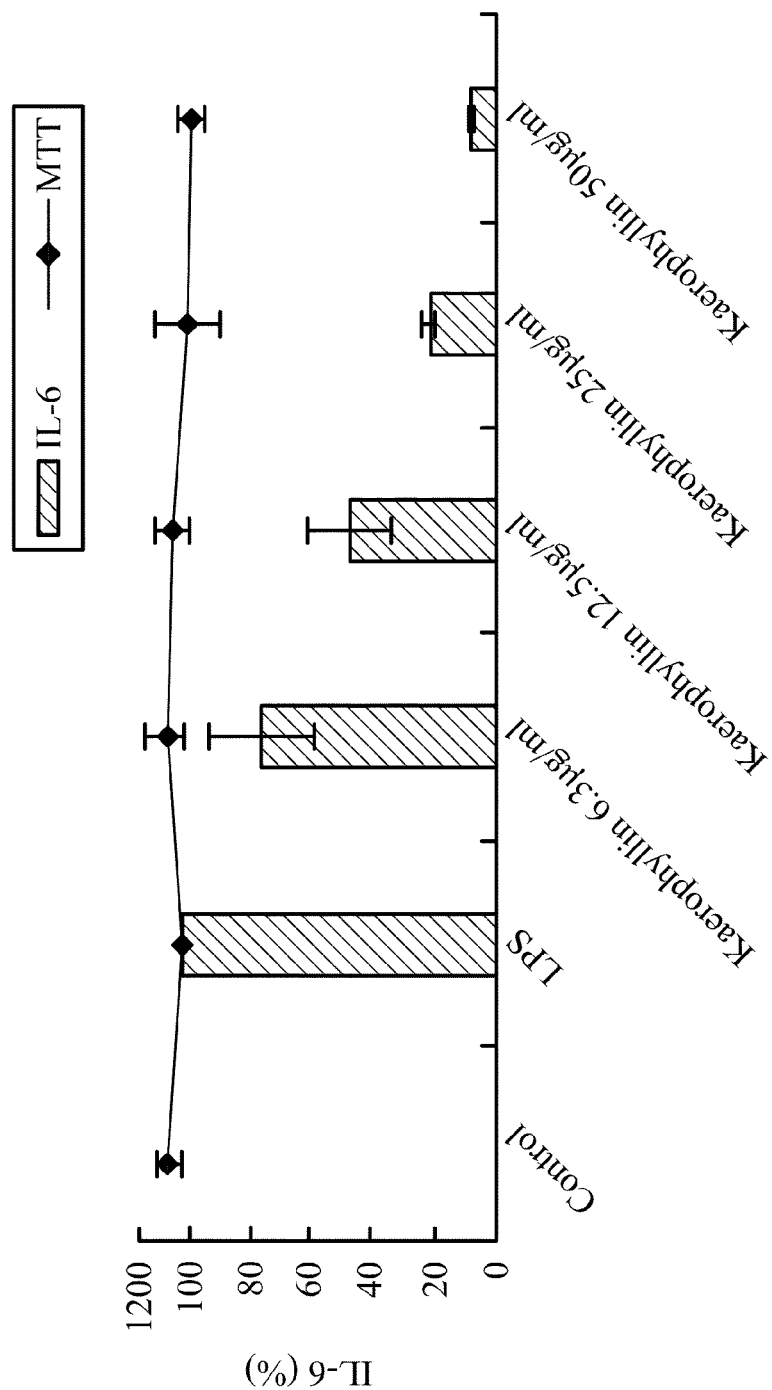
FIG. 14 is the inhibition of IL-6 in a U937 cell line by kaerophyllin.
Figure 15:
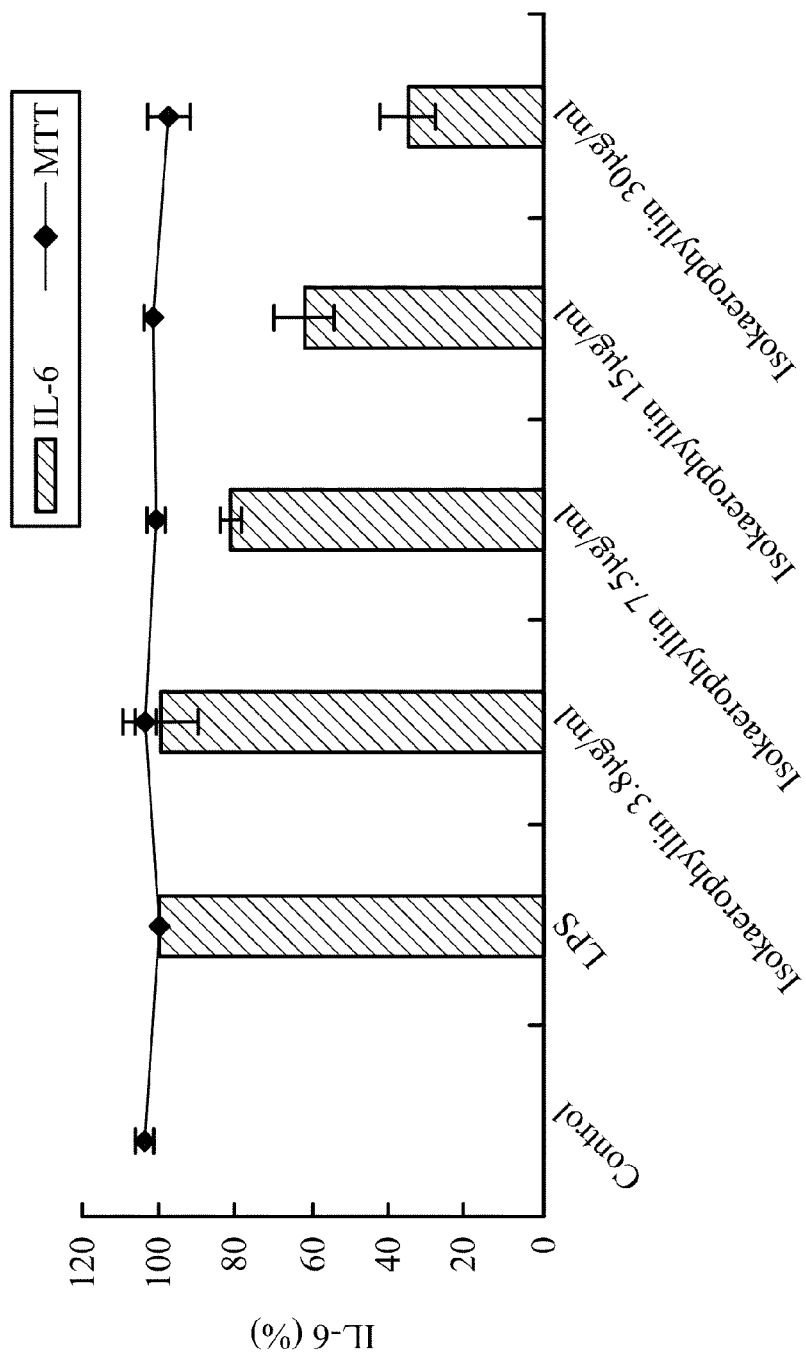
FIG. 15 is the inhibition of IL-6 in a U937 cell line by isokaerophyllin.

The results showed that kaerophyllin and the isomer had effects to inhibit the excretion of IL-6. The $IC_{50}$ value of kaerophyllin was 13±2 μg/ml (FIG. 14). The $IC_{50}$ value of isokaerophyllin was 24±6 μg/ml (FIG. 15).

EXAMPLE 15

Effect of the Ethanol Extract in an Enteritis Mouse Model

The BABL/c mice were categorized into 4 groups. Each group had 6 rats. One group was injected 50% ethanol and others were injected 1.75 mg of trinitrobenzene sulfonate (TNBS) (Sigma) into the colon (4 cm up from the anus). The TNBS-treated groups were immediately fed with 100 mg/kg of the extract (a) in Example 5 (i), 0.6 mg/kg of dexamethasone (DEX) and nothing, respectively. After 48 hours, the colon (6 cm up from the anus) of each mice was excised and the colon was immerged in PBS for 2 hours. The colon infusion was measured for the amounts of TNF-α, IL-6 and G-CSF. The inhibition of TNF-α, IL-6 and G-CSF was calculated based on the TNBS-treated group without being fed anything. The results are shown in Table 10, in which a negative value represents enhanced excretion of TNF-α, IL-6 and G-CSF.

TABLE 10

| Group | Inhibition of TNF-α (%) | Inhibition of IL-6 (%) | Inhibition of G-CSF (%) |
|---|---|---|---|
| 50% ethanol | 74 | 96 | 93 |
| 1.75 mg of TNBS | 0 | 0 | 0 |
| 100 mg/kg of the ethanol extract + 1.75 mg of TNBS | 50 | 43 | 60 |
| 0.6 mg/kg of DEX + 1.75 mg of TNBS | 9 | −55 | −38 |

EXAMPLE 16

Effect of *Bupleurum* Species on LPS Induced Inflammatory Response in a Mouse Model Six species of *Bupleurum* selected from Example 1 were individually pulverized and screened by a sieve with 5 meshes.

50 g of each ground *Bupleurum* and 400 mL of 50% ethanol aqueous solution were added into six 2 L round bottom flasks. The flasks were heated under reflux for 2 hours. The solution was collected. After dried and concentrated, the extracts (1)~(6) were obtained, which correspond to the Lines (b)~(g) of the *Bupleurum* species in Example 1.

BALB/c mice were fed with 1000 mg/kg of the extract (1) and 500 mg/kg of the extracts (2)~(6), respectively. After 2 hours, the mice were intraperitoneally injected with 1 mg/kg of LPS in PBS. Blood was collected after 1.5 hours. The concentration of TNF-α and IL-6 in the mice serum was quantified by ELISA (R& System®). The inhibition rates (%) of TNF-α and IL-6 in the serum were calculated based on the concentration of TNF-α and IL-6 in the serum of the mice without being fed the extracts. The results are shown in Table 11.

TABLE 11

| Extracts | Inhibition of TNF-α (%) | Inhibition of IL-6 (%) |
|---|---|---|
| Extracts (1) | 44 | −6 |
| Extracts (2) | 99 | 50 |
| Extracts (3) | 75 | 42 |
| Extracts (4) | 25 | 29 |
| Extracts (5) | 27 | 51 |
| Extracts (6) | 34 | 11 |

EXAMPLE 17

Identification of the *Bupleurum* by ITS Sequencing 0.5~1 g of the six *Bupleurum* (b)~(g) in Example 1 were individually pulverized with liquid nitrogen. The powder was poured into centrifugal tubes containing 7~10 ml of a CTAB buffer and well mixed. The tube was vibrated 30~60 minutes under 70° C. The tubes were added 5 ml of chloroform and well mixed. The tubes were centrifuged at 8,000 rpm for 5 minutes at 4° C. The supernatants were removed. The precipitates were centrifuged at 12,000 rpm for 20 minutes at 4° C. The supernatants were removed again. Each tubes was added 3 ml of 1.2M NaCl containing RNase. The tubes were vibrated for 30~60 min. at 37° C., added 3 ml of chloroform and well mixed. The tubes were centrifuged at 8,000 rpm for 5 min. at 4° C. The supernatants were moved to new 1.5 ml microcentrifuge tubes and added isopropanol of 0.6 times that of the volume. The tubes were put in a −20° C. refrigerator to precipitate overnight. After centrifuged, the precipitates were washed by 75% ethanol once and dried. The precipitates were resolved with 50 μl of TE. The solution was under PCR with primers to amplify the DNA sequences of the *Bupleurum* species. The DNA sequences of the *Bupleurum* (b)~(g) are shown in the sequence list in accordance with SEQ ID NOs. 1~6.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A pharmaceutical composition with an immunomodulating function consisting essentially of a therapeutically effective amount of a solvent extract of *bupleurum krlovianum, bupleurum pusillum, bupleurum longicaule, bupleurum salicifolium* or a combination thereof, wherein the solvent is hexane or ethanol-ethyl acetate.

* * * * *

SEQUENCE LISTING

<160> NUMBER OF SEQ ID NOS: 6

<210> SEQ ID NO 1
<211> LENGTH: 629
<212> TYPE: DNA
<213> ORGANISM: Bupleurum sp.

-continued

```
<400> SEQUENCE: 1
ggatcattgt cgaatcctga aacgaagagc gacccgagaa catgttttaa gacggggcca      60
gcggtsgtcg gcctcggcct gacggctgcg aaccctaggc cggggggctc ctagttgtgc     120
ccgccggccc aaaacctaac cgggcgcgga atgcgcaag gaaaccgaaa ctgaacagga      180
tgtctccgcc ccgtttgagg gggggtcgac atccttctga gaaacaaacg actctcggca    240
acggatatcc cggctctcgc atcgatgaag aacgtagcga aatgcgatac ttggtgtgaa    300
ttgcagaatc ccgtgaacca tcgagttttt gaacgcaagt tgcgcccgat gccattaggc    360
tgagggcacg tctgcctggg tgtcacgtaa agctttgccc ctccgcagct cgctcaaagc    420
gagtcggtgc tgttcggggg gacggaaatt gacctcccgt gcctcgtcgt gcggctggtt    480
taaaagagag tctccggaga tcggaaaacg caacattggt ggaatgcatt acgcacctct    540
tgccatcttg cgctgagccc gtttactctg tgagcaacag cgaccctttg gcgccgcccc    600
aggtgcgcgc tcgaactgtg accccaggt                                      629

<210> SEQ ID NO 2
<211> LENGTH: 629
<212> TYPE: DNA
<213> ORGANISM: Bupleurum krlovianum

<400> SEQUENCE: 2
ggatcattgt cgaatcctga atcgaagtgc gacccgagaa catgttttaa gacggggcca     60
gcggtcgtcg gcctcggcct gacggctgcg aaccctaggt cgggggggcgc ctagttgtgc   120 ctgccggccc aaaacctaac cgggcgcgga atgcgccaag gaaaccgaaa ctgaacagga    180
tgtctccgcc ccgtttgagg gggggtcatc atccttctga gaaacaaacg actctcggca    240
acggatatcc cggctctcgc atcgatgaag aacgtagcga aatgcgatac ttggtgtgaa    300
ttgcagaatc ccgtgaacca tcgagttttt gaacgcaagt tgcgcccgat gccattaggc    360
tgagggcacg tctgcctggg tgtcacgtaa agctttgccc ctccgcagct cgctcaaagc    420
gagtcgttga tgttcggggg gacggaaagt gacctcccgt gcctcgtcgt gcggctggtt    480
taaaagagag tctccggaga tcggaaaacg caacattggt ggaaggcatt acgcacctct    540
tgccatcttg cgctgagccc gtttactcca tgagcaacag cgaccctttg gcgccgcccc    600
aggtgagcgc tcgaactgtg accccaggt                                      629

<210> SEQ ID NO 3
<211> LENGTH: 629
<212> TYPE: DNA
<213> ORGANISM: Bupleurum longiradiatum
<220> FEATURE:
<221> NAME/KEY: misc_feature
<222> LOCATION: (107)
<223> OTHER INFORMATION: n is a, c, g, or t

<400> SEQUENCE: 3
ggatcattgt cgaatcctga atcgaagagc gacccgagaa catgttttaa gacggggcca     60
gcggtcgtcg gcctcggcct gacggctgcg aaccctaggc cggggntgc ctagttgtgc    120 ccgccggccc aaaacctaac cgggcgcgga atgcgccaag gaaaccgaaa ctgaacagga    180
tgtctccgcc ccgtttaagg gggggtcgac atccttctga gaaacaaacg actctcggca    240
acggatatcc cggctctcgc atcgatgaag aacgtagcga aatgcgatac ttggtgtgaa    300
ttgcagaatc ccgtgaacca tcgagttttt gaacgcaagt tgcgcccgat gycattaggc    360
tgagggcacg tctgcctggg tgtcacgtaa agctttgccc ctccgcagct cgctcaaatc    420
```

-continued

| | |
|---|---|
| gagtcgttgc tgttcggggg gacggaaatt gacctcccgt gcctcgtcgt gcggctggtt | 480 |
| taaaagagag cctccggaga tcggaaaacg caacattggt ggaaggcatt acgcacctct | 540 |
| tgccatcttg cgctgagccc gttyactctg tgagcaacag cgacccttg gcgccgcccc | 600 |
| aggcgcgcgc tcgaactgtg accccaggt | 629 |

<210> SEQ ID NO 4
<211> LENGTH: 629
<212> TYPE: DNA
<213> ORGANISM: Bupleurum sp.

<400> SEQUENCE: 4

| | |
|---|---|
| ggatcattgt cgaatcctga atcgaagacc gacccgagaa catgttttaa gacggggcca | 60 |
| gcggtcgtcg gcctcggcct gacggctgcg aaccctaggc cgggggggcgc ctagttgtgc | 120 |
| ccgccggccc aaaacctaac cgggcgcgga atgcgccaag gaaaccgaaa ctgaacagga | 180 |
| tgtctccgcc ccgtttgagg gggggtcgac atccttcaaa gaaacaaacg actctcggca | 240 |
| acggatatcc cggctctcgc atcgatgaag aacgtagcga aatgcgatac ttggtgtgaa | 300 |
| ttgcagaatc ccgtgaacca tcgagttttt gaacgcaagt tgcgcccgat gccattaggc | 360 |
| tgagggcacg tctgcctggg tgtcacgtat agctttgccc ctccgcagct cgctcaaagc | 420 |
| gagtcgttgc tgttcggggg gacggaaatt gacctcccgt gcctcgtcgt gcggctggtt | 480 |
| taaaagagag tctccggaga tcggaaaacg caacattggt ggaatgcatt acgcacctct | 540 |
| tgccatcttg cgctgagccc gtttactctg tgagcaacag cgacccttg gcgccgcccc | 600 |
| aggtgcgcgc tcgaactgtg accccaggt | 629 |

<210> SEQ ID NO 5
<211> LENGTH: 629
<212> TYPE: DNA
<213> ORGANISM: Bupleurum sp.

<400> SEQUENCE: 5

| | |
|---|---|
| ggatcattgt cgaatcctga atcgaagagc gacccgagaa catgttttaa gacggggcca | 60 |
| gcggtcgtcg gcctcggcct gacgtctgcg aaccctaggc cgggggggcgc ctagttgtgc | 120 |
| ccgccggccc aaaacctaac cgggcgcgga atgcgccaag gaaaccgaaa ctgaacagga | 180 |
| tgtctccgcc ccgtttgagg gggggtcgac atccttctga gaaacaaacg actctcggca | 240 |
| acggatatcc cggctctcgc atcgatgaag aacgtagcga aatgcgatac ttggtgtgaa | 300 |
| ttgcagaatc ccgtgaacca tcgagttttt gaacgcaagt tgcgcccgat gccattaggc | 360 |
| tgagggcacg tctgcctggg tgtcacgtaa agctttgccc ctccgcagct cgctcgaagc | 420 |
| gagtcgttgc tgttcggggg gacggaaagt gacctcccgt gcctcgtcgt gcggctggtt | 480 |
| taaaagagag cctccggaga tcggaaaacg caacattggt ggaaggcatt acgcacctct | 540 |
| tgccatcttg cgctgagccc gtttactctg tgagcaactg cgacccttg gcgccgcccc | 600 |
| aggtgcgcgc tcgaactgtg accccaggt | 629 |

<210> SEQ ID NO 6
<211> LENGTH: 629
<212> TYPE: DNA
<213> ORGANISM: Bupleurum sp.

<400> SEQUENCE: 6

| | |
|---|---|
| ggatcattgt cgaatcctga atcgaagagc gacccgagaa catgttttaa gacggggcca | 60 |
| gcggtcgtcg gcctcggcct gacggctgcg aaccctaggc cgggggggcgc ctagttgtgc | 120 |

| | | | | | |
|---|---|---|---|---|---|
| ccgccgaccc | aaaacctaac | cgggcgcgga | atgcgccaag | gaaaccgaaa | ctgaacagga | 180 |
| tgtctccgcc | cctttcgagg | ggggtcgac | atccttctga | aaaacaaacg | actctcggca | 240 |
| acggatatcc | cggctctcgc | atcgatgaag | aacgtagcga | aatgcgatac | ttggtgtgaa | 300 |
| ttgcagaatc | ccgtgaacca | tcgagttttt | gaacgcaagt | tgcgcccgat | gccattaggc | 360 |
| cgagggcacg | tctgcctggg | tgtcacgtaa | agctttgccc | ctccgcagct | cgctcaaagc | 420 |
| gagtcgttgc | tctcgtgggg | gacggaaatt | gacctcccgt | gcctcgtcgt | gcggctggtt | 480 |
| taaaagagag | tctccgggga | tcggaaaacg | caacattggt | ggaaggcatt | acgcacctct | 540 |
| tgccatcttg | cgctgagccc | gtttactctg | tgagcaacag | cgacccttg | gcgccgcccc | 600 |
| aggtgcgcgc | tcgaactgtg | accccaggt | | | | 629 |